| United States Patent [19] | [11] Patent Number: 4,837,333 |
| --- | --- |
| Manley et al. | [45] Date of Patent: Jun. 6, 1989 |

[54] SUBSTITUTED ALKYLIDENE IMIDAZOLES

[75] Inventors: Paul W. Manley, Monks Risborough; Roderick A. Porter, High Wycombe, both of United Kingdom; Mun F. Lai, Singapore, Singapore

[73] Assignee: G. D. Searle & Co., Chicago, Ill.

[21] Appl. No.: 49,491

[22] Filed: May 14, 1987

[51] Int. Cl.$^4$ .......................................... C07D 233/60
[52] U.S. Cl. .................................... 548/341; 540/603; 546/187; 546/211; 548/335; 548/336
[58] Field of Search ............. 548/335, 336, 341; 546/220, 187, 211; 540/603

[56] References Cited

U.S. PATENT DOCUMENTS

| 4,243,671 | 1/1981 | Harris et al. | 514/396 |
| 4,284,641 | 8/1981 | Thorogood | 514/396 |
| 4,357,340 | 11/1982 | Thorogood | 514/396 |
| 4,416,895 | 11/1983 | Thorogood | 514/396 |

FOREIGN PATENT DOCUMENTS 2025946  1/1980  United Kingdom ............... 514/396

*Primary Examiner*—M. C. Lee
*Assistant Examiner*—Kurt G. Briscoe
*Attorney, Agent, or Firm*—J. Timothy Keane; Paul D. Matukaitis

[57] ABSTRACT

This disclosure relates to a class of novel substituted alkylidene imidazole derivatives and pharmaceutically acceptable salts thereof. The disclosure further describes pharmaceutical compositions containing such compounds and to the use of such compounds and compositions as agents for selectively inhibiting the action of the enzyme thromboxane synthetase.

2 Claims, No Drawings

SUBSTITUTED ALKYLIDENE IMIDAZOLES

This is a continuation of application Ser. No. 764,689, filed 8/12/85, now abandoned, which is a continuation-in-part of application Ser. No. 681,036, filed Dec. 12, 1984, now abandoned.

This invention relates to a class of novel compounds comprising substituted alkylidene imidazole derivatives and pharmaceutically acceptable salts thereof. The present invention further relates to pharmaceutical compositions containing such compounds and to the use of such compounds and compositions as agents for selectively inhibiting the action of the enzyme thromboxane synthetase. Certain compounds and compositions of the present invention may be particularly useful in treating diseases which involve platelet dysfunction or platelet hyperactivity, such as cerebrovascular disease, ischaemic heart disease, diabetic retinopathy, angina, peripheral vascular disease and myocardial infarction.

BACKGROUND OF THE INVENTION

The discovery of thromboxane $A_2$ ($TxA_2$) and prostacyclin ($PGI_2$), has increased the understanding of vascular haemostasis. Platelets transform arachidonic acid initially into prostaglandin endoperoxides, via an enzyme, cyclooxygenase, and subsequently into $TxA_2$, by an enzyme, thromboxane synthetase. $TxA_2$ is a potent vasoconstrictor and proaggregatory substance, and as such, its actions are directly opposed to $PGI_2$. When platelets are stimulated by thrombin, collagen, ADP and adrenaline, the platelets release and metabolise endogenous arachidonic acid to $TxA_2$. This endogenous $TxA_2$ appears to play an essential role in a second irreversible phase of ADP- and collagen- induced platelet aggregation. In addition to aggregating platelets, $TxA_2$ is a potent vasoconstrictor and thus the continuous generation of $TxA_2$ by platelets adhering to damaged arterial walls results in localised vasoconstriction of the arteries.

$PGI_2$ is a powerful vasodilator and potent anti-aggregatory agent, effective in preventing platelets from aggregating and in reversing platelet aggregation by dissipating platelet clumps. $PGI_2$ is synthesised from prostaglandin endoperoxides by an enzyme, prostacyclin synthetase, located in the endothelial layer of blood vessels and in circulating polymorphonuclear leukocytes.

Normal morphological interaction between platelets and vessel walls provides for the transfer of prostaglandin endoperoxides from platelets to endothelial cells thereby increasing $PGI_2$ production and preventing platelet deposition on vessel walls. Thus when endothelial prostacyclin synthetase is inactivated, for example, by lipid peroxides, or when endothelium becomes detached exposing the underlying connective tissues (i.e., collagen) to platelets, or when polymerising fibrin prevents the interaction between platelets and endothelial cells, arterial thrombosis may develop.

Thus, $TxA_2$ has been implicated as a causative agent in thrombus formation, myocardial infarction, stroke, variant angina and peripheral vascular disease. Effective in vivo inhibition of platelet thromboxane synthetase is likely to be beneficial for two major reasons: (i) $TxA_2$ formation in response to platelet aggregatory stimuli is blocked, reducing platelet reactivity and vascular spasm, and (ii) increased availability of prostaglandin endoperoxides as a substrate for prostacyclin synthetase increases the production of the platelet inhibitory and vasodilator $PGI_2$ in the blood and vessel wall. Therefore, the $PGI_2/TxA_2$ balance is shifted decisively in favour of $PGI_2$.

A $PGI_2/TxA_2$ imbalance is also believed to be a contributory factor in migraine. The migraine headache is associated with a pre-headache reduction of cerebral blood flow followed by dilatation in both the intra- and extra-cerebral vascular areas during the headache phase. Prior to the headache, blood levels of 5-hydroxytryptamine are elevated, suggesting the occurrence of in vivo aggregation and release of the amine from the platelet stores. Migraine sufferers also tend to have hyperactive blood-platelets and it has been postulated that an abnormality of platelet function is not only a major factor in the pathogenesis of migraine attacks but a primary cause (E. Hanington, Lancet, (1978), 8084, 501). Therefore selective inhibition of thromboxane synthetase may be beneficial in migraine therapy.

Platelets obtained from some patients with diabetes mellitus are hyperactive, exhibiting enhanced in vitro $TxA_2$ generation and aggregation when stimulated by a variety of aggregatory agents. Such patients have a high frequency of vascular complications such as retinopathy, coronary heart disease and peripheral arterial occlusive disease. A $PGI_2/TxA_2$ imbalance is probably responsible for the microvascular complications of diabetes and consequently a thromboxane synthetase inhibitor may have clinical utility in the therapy of these complications.

Aspirin and other non-steroidal anti-inflammatory drugs (e.g. indomethacin, sulphinpyrazone) inhibit the enzyme cyclooxygenase and therefore inhibit $PGI_2$ production as well as $TxA_2$ production. A drug which specifically inhibits $TxA_2$ formation while leaving $PGI_2$ biosynthesis unimpaired, should therefore display advantages in the treatment of conditions involving an imbalance of $PGI_2/TxA_2$ over the currently available cyclooxygenase inhibitors.

U.S. Pat. No. 4,243,671 describes the use of 1-(3-phenyl-2-propenyl)-1H-imidazole and its hydrochloride salt as an inhibitor of thromboxane synthetase and as an inhibitor of arachidonic acid-induced platelet aggregation and bronchoconstriction.

SUMMARY OF THE INVENTION

The compounds of the present invention include substituted alkylidene imidazole derivatives represented by the formula

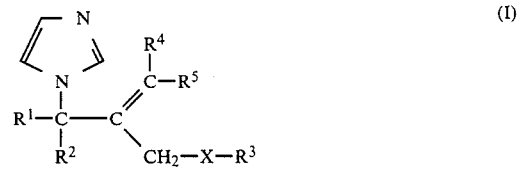

(I)

wherein
$R^1$ and $R^2$ are independently hydrogen or $C_1$–$C_{10}$ alkyl;
$R^3$ is selected from the group consisting of $C_1$–$C_{10}$ alkyl; $C_2$–$C_{10}$ alkenyl; $C_2$–$C_{10}$ alkynyl; substituted $C_1$–$C_{10}$ alkyl, $C_2$–$C_{10}$ alkenyl and $C_2$–$C_{10}$ alkynyl wherein the substituent is selected from the group consisting of —$OR^7$, —$S(=O)_mR^7$ wherein m is from 0 to 2, —$NR^7R^8$, —$COOR^7$, —$CONR^7R^8$ and —$COR^7$; and a —$CH_2R^6$ group wherein $R^6$ is phenyl or substituted phenyl containing one or more substituents selected from the class comprising of halogen, $-OR^7$, $-S(=O)_mR^7$ wherein m is from 0 to 2, $-COR^7$, $-COOR^7$, $-CONR^7R^8$ or $-NR^7R^8$; wherein each $R^7$ and $R^8$ is independently hydrogen or $C_1-C_4$ alkyl, or $R^7$ and $R^8$ taken together represent a $C_4-C_6$ alkylene chain so as to form a cyclic ring with the adjacent nitrogen atom; X is oxy, thio, a $-CH_2-$ or a $-NR^9-$ group, wherein $R^9$ is hydrogen, $C_1-C_4$ alkyl or benzyl;

$R^4$ is a group represented by $W^1$ or $W^2$ wherein $W^1$ is hydrogen or $C_1-C_{10}$ alkyl and $W^2$ is $C_1-C_{10}$ alkyl; $C_2-C_{10}$ alkenyl; $C_2-C_{10}$ alkynyl; substituted $C_1-C_{10}$ alkyl, $C_2-C_{10}$ alkenyl, and $C_2-C_{10}$ alkynyl wherein the substituent is selected from the group consisting of halogen, $-OR^7$, $-S(=O)_mR^7$ wherein m is from 0 to 2, $-NR^7R^8$, $-COOR^7$, $-CONR^7R^8$, wherein each $R^7$ and $R^8$ is independently hydrogen or $C_1-C_4$ alkyl, or $R^7$ and $R^8$ taken together represent a $C_4-C_6$ alkylene chain so as to form a cyclic ring with the adjacent nitrogen atom; alkyl, alkenyl, alkynyl or substituted alkyl, alkenyl and alkynyl group represented by $W^2$ interrupted with an oxy, thio or $-NR^9-$ group wherein $R^9$ is hydrogen, $C_1-C_4$ alkyl, or benzyl; and phenyl, benzyl, substituted phenyl and substituted benzyl containing one or more substituents selected from the class consisting of halogen, $-OR^7$, $-S(=O)_mR^7$ wherein m is from 0 to 2, $-COR^7$, $-COOR^7$, $-CONR^7R^8$, $-NR^7R^8$, wherein each $R^7$ and $R^8$ is independently hydrogen or $C_1-C_4$ alkyl or $R^7$ and $R^8$ taken together represent a $C_4-C_6$ alkylene chain so as to form a cyclic ring with the adjacent carbon or nitrogen atom;

$R^5$ is a group represented by $W^1$ or $W^2$ provided that if $R^4$ is $W^1$, $R^5$ is $W^2$ and if $R^4$ is $W^2$, $R^5$ is $W^1$; and pharmaceutically acceptable salts thereof.

As illustrated above, the substituted alkylidene imidazole derivatives of the present invention contain a polysubstituted carbon-carbon double-bond and thus the scope of this invention includes both the individual E- and Z-isomers as well as mixtures of the E- and Z-isomers of the compounds represented by formula (I). In addition, the compounds of formula (I) may contain one or more asymmetric centres, thus the scope of this invention includes all stereoisomers represented herein, including but not limited to enantiomeric forms, designated racemates, and diastereomers.

The present invention further relates to pharmaceutical compositions containing such compounds and/or salts. Certain compounds represented by formula (I), pharmaceutically acceptable acid addition salts thereof and compositions containing such compounds and/or salts have been found to selectively inhibit the action of the enzyme thromboxane synthetase without significantly affecting the action of the cyclooxygenase or prostacyclin synthetase enzymes. Therefore certain compounds and salts thereof of the present invention and compositions containing such compounds and salts are useful in the treatment of a variety of clinical conditions which are characterised by an imbalance of prostacyclin/thromboxane $A_2$. These conditions may include, for example, cerebrovascular disease, ischaemic heart disease, diabetic retinopathy, angina, peripheral vascular disease and myocardial infarction.

DETAILED DESCRIPTIONS OF THE INVENTION

In accordance with the present invention the groups $R^1$ and $R^2$ in the compounds represented by formula (I) are preferably hydrogen or methyl.

$R^3$ may represent a straight or branched chain alkyl, alkenyl or alkynyl group. Such groups may contain up to ten carbon atoms, preferably up to eight carbon atoms in the case of a straight chain and up to ten carbon atoms in the case of a branched chain. The alkyl, alkenyl or alkynyl groups represented by $R^3$ may be substituted with a $OR^7$ or $S(=O)_mR^7$ group wherein $R^7$ is preferably hydrogen or methyl and m is from 0 to 2. The group $R^3$ may also represent a $-CH_2R^6$ group wherein $R^6$ is phenyl or substituted phenyl. Examples of groups represented by $R^3$ include but are not limited to benzyl, 4-fluorobenzyl, 4-methoxybenzyl, 4-carboxybenzyl, 4-ethoxycarbonylbenzyl, 4-(t-butoxy)carbonylbenzyl, 4-dimethylaminocarbonylbenzyl, 4-dimethylaminobenzyl, and the like.

In accordance with the present invention, $R^4$ is preferably hydrogen or methyl.

$R^5$ may represent $C_1-C_{10}$ alkyl, $C_2-C_{10}$ alkenyl or a $C_2-C_{10}$ alkynyl, any of which may be interrupted with a thio($-S-$), oxy($-O-$) or a $-NR^9-$ group (e.g. ethoxyethyl). Such groups preferably contain of from four to six carbons if $R^5$ is a straight chain alkyl, alkenyl or alkynyl group and six to eight carbons if $R^5$ is a branched chain alkyl, alkenyl or alkynyl group. Compounds of formula (I) wherein the alkyl, alkenyl, alkynyl or substituted alkyl, alkenyl or alkynyl group represented by $R^5$ is interrupted with an oxy, thio, or $-NR^9-$ moiety (wherein $R^9$ preferably represents hydrogen, methyl or benzyl), are preferred when X represents a $-CH_2-$ group. Preferred compounds are those in which $R^5$ is substituted with a group selected from $OR^7$, $COR^7$, $COOR^7$, $CONR^7R^8$, wherein each $R^7$ or $R^8$ is as hereinbefore defined. Particularly preferred substituent groups are $COOR^7$ and $CONR^7R^8$.

A particularly preferred group of compounds of formula (I) are compounds wherein $R^5$ represents a $C_4-C_8$ straight chain or branched chain alkyl, alkenyl or alkynyl group substituted with a group $COOR^7$, $CONR^7R^8$ wherein each $R^7$ or $R^8$ is defined above. Examples of such groups include, but are not limited to, $(CH_2)_5COOH$, $(CH_2)_5COOCH_2CH_3$, $(CH_2)_5COOCH_2C(CH_3)_3$, $(CH_2)_4C(CH_3)_2COOH$, E- and Z- $(CH_2)_3CH=CHCOOH$, E- and Z- $(CH_2)_3CH=CHCOOCH_2CH_3$ and the like.

$R^5$ may also represent a phenyl or substituted phenyl having one or more substituents selected from the class consisting of fluoro, chloro, bromo, $OR^7$, $S(=O)_mR^7$ wherein n is from 0 to 2, $COR^7$, $COOR^7$, $CONR^7R^8$, or $NR^7R^8$ wherein each $R^7$ or $R^8$ is defined above. Preferably $R^5$ represents substituted phenyl having one or more substituents selected from the class consisting of chloro $OR^7$, $SR^7$, $COOR^7$ and $CONR^7R^8$. Examples of such preferred substituted phenyl groups include, but are not limited to, 4-methoxyphenyl, 4-methylthiophenyl, 4-carboxyphenyl, 4-butoxycarbonylphenyl, 3-carboxyphenyl, 4-methylaminocarbonylphenyl, 4-dimethylaminocarbonylphenyl, 3-methoxy-4-ethoxycarbonylphenyl, and the like.

In accordance with the present invention, X preferably represents an oxy ($-O-$), thio ($-S-$) or a $-CH_2-$ group, and most preferably a $-CH_2-$ group.

In a preferred embodiment of the present invention, $R^1$, $R^2$, $R^3$ and $R^4$ are as defined above; $R^5$ represents a $C_{1-10}$ alkyl, alkenyl or alkynyl group substituted with a group selected from $OR^7$, $COOR^7$, $CONR^7R^8$ or $COR^7$, wherein each $R^7$ and $R^8$ is defined above and X represents oxy, thio, or $—CH_2—$ group.

In an alternative preferred embodiment of the invention: $R^1$, $R^2$, $R^3$ and $R^4$ are as defined above; and $R^5$ represents a phenyl ring optionally substituted with one or more groups selected from halogen, $OR^7$, $S(=O)_mR^7$, (m=0-2), $COOR^7$, $CONR^7R^8$ or $NR^7R^8$ wherein each $R^7$ or $R^8$ is defined above.

A more preferred class of compounds are represented by the formula

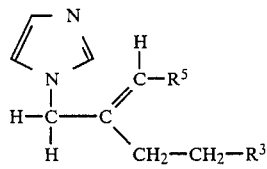
(II)

wherein $R^3$ and $R^5$ are above-defined. A most preferred embodiment is a class of compounds represented by formula (II) wherein $R^3$ is a $C_5$–$C_{10}$ alkyl, or a $—CH_2R^6$ group; and $R^5$ is $C_5$–$C_{10}$ alkyl, $C_5$–$C_{10}$ alkylcarboxyl, phenyl or substituted phenyl.

The alkyl, alkenyl and alkynyl group specified herein are straight chain or branched chain hydrocarbon moieties containing up to ten carbon atoms. Illustrative alkyl radicals include methyl, ethyl, propyl, isopropyl, butyl, isobutyl, sec-butyl, tert-butyl, pentyl, neopentyl, hexyl, isohexyl, heptyl, decyl and like monovalent, saturated acyclic, straight- or branched-chain, hydrocarbon groupings of the empirical formula

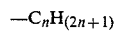

wherein n represents a positive integer less than 11. Representative alkenyl and alkynyl radicals are groups which can be thought of as derived from polycarbon alkyl radicals by displacement of two or more hydrogens to give rise to a double bond or a triple bond, respectively. Illustrative alkenyl radicals are vinyl, 1-propenyl, 2-propenyl, 1-methyl-1-propenyl, 2-methyl-1-propenyl, 1-butenyl, 2-butenyl, 3-butenyl, and the like. Illustrative alkynyl radicals are ethynyl, 1-propynyl, 2-propynyl, 1-butynyl, 2-butynyl, 3-butynyl, and the like.

The term "substituted phenyl" and "substituted benzyl" as used herein represent a phenyl radical or benzyl radical respectively, preferably having from one to three substituents, although as many as five substituents are within the purview of this invention. Among these substituents include carboxyl, alkylcarboxyl, amide, $C_1$–$C_4$ alkoxy, $—NHCOO(C_1$–$C_4$ alkyl), $C_1$–$C_4$ alkylsulfinyl, $C_1$–$C_4$ alkylthio, $C_1$–$C_4$ alkyl) amino, amido, halogen, preferably fluoro, chloro or bromo, and the like.

The term "substituted alkyl, alkenyl or alkynyl" refers to alkyl, alkenyl or alkynyl groups wherein a hydrogen from a carbon is replaced by a substituent. Among these substituents include alkylcarboxyl, amide, $C_1$–$C_4$ alkoxy, $—NHCOO(C_1$–$C_4$ alkyl), $C_1$–$C_4$ alkylthio, amino, $C_1$–$C_4$ alkylamino, di-($C_1$–$C_4$ alkyl)amino, halogen, preferably chloro or bromo, and the like.

The term "pharmaceutically acceptable salts" refers to salts derived from physiologically acceptable acids. Such physiologically acceptable acids include but are not limited to hydrochloric, hydroiodic, hydrobromic, phosphoric, sulphuric, toluenesulphonic, acetic, maleic, benzoic citric, fumaric, gluconic, lactic, malic, nitric, saccharic, succinic, tartaric and the like.

The compounds represented by formula (I) may be preferably prepared by a Wadsworth-Emmons reaction of a ketone of the formula

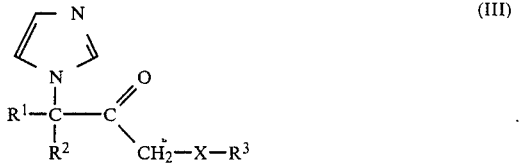
(III)

wherein $R^1$, $R^2$, $R^3$ and X are as hereinbefore defined; with an alkali metal salt (e.g. potassium) of a dialkylphosphonate of the formula

(IV)

wherein $R^{10}$ is a $C_1$–$C_4$ alkyl group, preferably methyl or ethyl, and $R^4$ and $R^5$ are as hereinbefore defined, obtained by the reaction of a dialkylphosphonate of formula (IV) with potassium t-butoxide, or by a Wittig reaction employing a phosphorane compound of the formula

(V)

wherein $R^{11}$ represents a phenyl group or an alkyl group containing from 1 to 10 carbon atoms, preferably octyl, and $R^4$ and $R^5$ are as hereinbefore defined. The Wittig reaction is preferably carried out in an inert organic solvent such as diethyl ether, tetrahydrofuran, dimethylformamide or dimethylsulphoxide and at a temperature within a range of from 10° C. to the reflux temperature of the solvent.

The dialkylphosphonates of formula (IV) and the phosphorane compounds of formula (V) may be prepared using known conventional methods.

The ketones of formula (III) may be prepared by the oxidation of the hydroxymethylene group of a compound of the formula

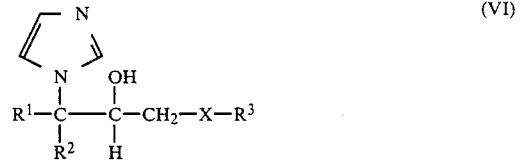
(VI)

wherein $R^1$, $R^2$, $R^3$ and X are as hereinbefore defined. This oxidation may be carried out, for example, utilizing the method described by D. Swern et al, *J. Org. Chem.*, (1978), 43, 2480 employing a dimethylsulphoxide-oxalyl chloride complex in dichloromethane at $-50°$ C.

The compounds of formula (VI) may be prepared by the reaction of a substituted oxirane of the formula $$R^1-C\underset{R^2}{\overset{O}{\diagdown\!\!\!\!\!\diagup}}C\underset{H}{\overset{|}{-}}CH_2-X-R^3 \quad (VII)$$

wherein $R^1$, $R^2$, $R^3$ and X are as hereinbefore defined; with imidazole, or an alkali metal salt of imidazole, such as the sodium salt, in a suitable polar solvent such as acetonitrile or dimethylformamide within temperature range of 60°–120° C.

The oxiranes of formula (VII) wherein X is oxygen or sulfur and $R^1$, $R^2$ and $R^3$ are defined as hereinbefore; may be obtained by reacting an epihalohydrin of the formula $$R^1R^2C\overset{O}{\diagdown\!\!\!\!\!\diagup}CH-CH_2-Y^1 \quad (VIII)$$

wherein $Y^1$ is chloro or bromo; with a compound of the formula $$HX-R^3 \quad (IX)$$

wherein X is oxygen or sulfur and $R^3$ is defined as hereinbefore; preferably in the presence of a suitable base such as sodium hydride, and in an aprotic solvent such as tetrahydrofuran.

The oxiranes of formula (VII), wherein X is a —$CH_2$— group, may be prepared by reacting alkenes of the formula $$R^1R^2C=CH-CH_2-R^3 \quad (X)$$

wherein $R^1$, $R^2$ and $R^3$ are hereinbefore defined with m-chloroperoxybenzoic acid in an inert solvent such as dichloromethane. Compounds of formula (X) may be prepared by reacting haloalkenes of formula $$R^1R^2C=CH-CH_2-Y^1 \quad (XI)$$

wherein $R^1$, and $R^2$ are defined as hereinbefore and $Y^1$ is as herein defined with a Grignard reagent, $R^3MgY^2$, wherein $R^3$ is as hereinbefore defined and $Y^2$ represents chloro, bromo or iodo; in a suitable solvent such as diethyl ether or tetrahydrofuran.

The allylic halides of formula (X) wherein $Y^1$ is chloro may be prepared by reacting the corresponding allylic alcohol of the formula $$R^1R^2C=CH-CH_2OH \quad (XII)$$

wherein $R^1$, and $R^2$ are as hereinbefore defined; with either a mixture of triphenylphosphine and carbon tetrachloride or N-chlorosuccinimide and methyl sulphide.

The allylic alcohols of formula (XI) may be obtained by the reduction of a corresponding α,β-unstaturated acid of the formula $$R^1R^2C=CH-COOH \quad (XIII)$$

wherein $R^1$ and $R^2$ are as hereinbefore defined; using a suitable reducing agent, such as aluminium hydride or diisobutylaluminium hydride, in an inert solvent such as tetrahydrofuran.

The α,β-unsaturated acids of formula (XIII) may be prepared by the hydrolysis of the corresponding ethyl esters which are readily obtained by a Wadsworth-Emmons reaction of an appropriate ketone and triethyl phosphonoacetate in the presence of a suitable base, such as potassium t-butoxide.

The ketones of formula (III) wherein $R^1$ and $R^2$ independently represent $C_1$–$C_{10}$ alkyl and X represents oxy, thio or —$NR^9$— may be prepared by the reaction of an ester of the formula $$\underset{R^2}{\overset{\displaystyle\left\lceil\!\!\begin{array}{c}N\\\phantom{x}\\N\end{array}\!\!\right\rceil}{\underset{|}{R^1-\overset{|}{C}-COOR^{12}}}} \quad (XIV)$$

wherein $R^1$ and $R^2$ independently represent $C_1$–$C_{10}$ alkyl and $R^{12}$ represents a $C_1$–$C_4$ alkyl group, and the anion generated from the reaction of the tin derivative of the formula $$(R^{13})_3-Sn\ CH_2XR^3 \quad (XV)$$

wherein X and $R^3$ are as herein defined and $R^{13}$ represents a phenyl group or a $C_1$–$C_6$ alkyl group, preferable butyl, with a suitable base such as n-butyllithium in an aprotic solvent such as tetrahydrofuran at −78° C.

Compounds of formula (XV) wherein X represents thio, oxy, or a —$NR^9$— group, and $R^3$, $R^9$ and $R^{13}$ are as herein defined may be prepared by the reaction of a compound of the formula (IX) wherein X is thio, oxy or a —$NR^9$— group and $R^3$ is as herein defined; with tributyl(iodomethyl)stannane utilizing the method described by W. C. Still, *J. Amer. Chem. Soc.*, (1978), 100, 1481.

Compounds of formula (IX) wherein $R^1$, $R^2$ and $R^{12}$ are as herein defined; may be obtained by reacting a haloester of the formula $$R^1\overset{\overset{\displaystyle Y^2}{|}}{\underset{\underset{\displaystyle R^2}{|}}{C}}-COOR^{12} \quad (XVI)$$

wherein $R^1$, $R^2$ and $R^{12}$ are defined as hereinbefore and $Y^2$ represents chloro, bromo or iodo; with imidazole, or an alkali metal salt of imidazole, such as the sodium salt, in a suitable polar solvent such as dimethylformamide in the presence of an excess of a base such as anhydrous potassium carbonate within a temperature range of 50°–100° C.

Compounds of formula (XV) wherein $Y^2$ is bromo may be prepared by the Hell-Volhard-Zelinskii reaction of the corresponding unsubstituted acids utilizing bromine in the presence of phosphorous tribromide followed by esterification.

Ketones of formula (II) wherein both $R^1$ and $R^2$ represent $C_1$–$C_{10}$ alkyl and X represents a —$CH_2$— group may be prepared by the reaction of an ester of the formula (XIII) with a Grignard reagent, $R^3CH_2CH_2MgY^2$, wherein $R^3$ and $Y^2$ are as hereinbefore defined, in a suitable solvent such as diethyl ether or tetrahydrofuran.

The pharmaceutically acceptable acid addition salts of the compounds of the present invention may be prepared by conventional procedures, e.g. by reacting the free base in a suitable solvent, e.g. diethylether or ethanol, with a solution containing one equivalent of the desired acid in a suitable solvent, e.g. diethylether or ethanol. The salt generally precipitates from solution or is recovered by evaporation of the solvent.

As previously mentioned, certain compounds represented by formula (I), pharmaceutically acceptable acid addition salts thereof and compositions containing such compounds and/or salts have been found to selectively inhibit the action of the enzyme thromboxane synthetase without significantly affecting the action of the cyclooxygenase or prostacyclin synthetase enzymes. The ability of the compounds and compositions of the present invention to selectively inhibit the enzyme thromboxane synthetase is illustrated using the following in vitro assays:

(i) inhibition of the generation of thromboxane $A_2$ as determined by radioimmunoassay of its stable metabolite, thromboxane $B_2$ (New England Nuclear, Thromboxane $B_2$ [$^3$H] RIA kit, Catalogue No. NEK 007); and (ii) effect on the production of prostacyclin in cultured endothelial cells as determined by radioimmunoassay of its stable metabolite, 6-keto $PGF_{1\alpha}$ (New England Nuclear, 6-keto $PGF_{1\alpha}$ RIA kit, Catalogue No. NER 008).

Certain compounds of the present invention, in particular compounds wherein X is a —$CH_2$— group, have been shown to be effect in selectively inhibiting the enzyme thromboxane synthetase in vivo. These compounds or salts thereof may be administered by any suitable route, preferably in the form of a pharmaceutical composition adapted to such route, and in a dose effective for the treatment intended. Accordingly, the invention provides a class of novel pharmaceutical compositions comprising one or more of such compounds or salts thereof in association with one or more non-toxic, pharmaceutically acceptable carriers and/or diluents and/or adjuvants and if desired other active ingredients. These compositions may for example be administered orally or by injection.

For oral administraton, these pharmaceutical composition may be in the form of, for example, a tablet, capsule, suspension or liquid. The pharmaceutical compositions are preferably made in the form of a dosage unit contained in a particular amount of the active ingredient. Examples of such dosage units are tablets or capsules. These may with advantage contain an amount of active ingredient from about 5 to 250 mg preferably from about 25 to 150 mg. A suitable daily dose for a mammal may vary widely depending on the condition of the patient and other factors. However, a dose of from about 0.1 to 300 mg/kg body weight, particularly from about 1 to 100 mg/kg body weight may be appropriate.

The active ingredient may also be administered by injection as a composition wherein, for example, saline, dextrose or water may be used as a suitable carrier. A suitable daily dose is from about 0.1 to 100 mg per kg body weight injected per day in multiple doses depending on the disease being treated. A preferred daily dose would be from about 1 to 30 mg/kg body weight.

As indicated, the dose administered and the treatment regimen will be dependent, for example, on the disease, the severity thereof, on the patient being treated and his response to treatment and therefore may be widely varied. As used herein, the term "therapeutically effective" amount of a compound of the present invention refers to that dose administered to treat the disease condition. Such therapeutically effective amounts are readily ascertained by one of ordinary skill in the art.

The pharmaceutical compositions may be prepared by techniques well known in the art and described, inter alia, in Remington's Pharmaceutical Science, Mach Publishing Co., Easton, Penn., 1965.

The following Examples are intended to further illustrate the present invention and not to limit the invention in spirit or scope.

EXAMPLE 1

Ethyl 4-[3-(1H-imidazol-1-yl)-2-[[(4-methoxyphenyl)methoxy]methyl]-1propenyl]benzoate (E- and Z-isomers)

(a) 2,3-Epoxypropyl-4-methoxybenzyl ether

A solution of 4-methoxybenzyl alcohol (800 g, 5.8 mol) in dry tetrahydrofuran (1200 ml) was added dropwise to a stirred slurry of sodium hydride (280 g of a 60% dispersion in oil, 7.0 mol) in dry tetrahydrofuran (600 ml) at $-5°$ C. and under a gentle stream of dry nitrogen. The resulting slurry was allowed to warm up to room temperature and stirred until hydrogen evolution ceased. The resulting slurry containing sodium alkoxide was cooled to $-5°$ C., and treated with epibromohydrin (860 g, 6.3 mol) at a rate so as to maintain the temperature of the reaction mixture below 5° C. The reaction mixture was allowed to warm gradually to room temperature and was stirred for an additional 12 hours. The reaction mixture was filtered and washed with methanol. The filtrate and washings were combined and evaporated to dryness under reduced pressure to yield a crude product (250 g). The crude product was purified by column chromatography (silica gel, chloroform) to yield 2,3-epoxypropyl-4-methoxybenzyl ether as a pale yellow oil having the following structural characteristics:

$^1$H-NMR (δ-CDCl$_3$): 2.70 (m, 2H), 3.20 (m, 1H), 3.65 (m, 2H), 3.37 (s, 3H), 4.73 (s, 2H) and 7.15 (q, 4H).

(b) α[[(4-methoxyphenyl)methoxy]methyl]-1H-imidazole-1-ethanol 2,3-Epoxypropyl-4-methoxybenzyl ether (100 g, 0.515 mol) in dry tetrahydrofuran (200 ml) was treated with imidazole (44.4 g, 0.653 mol) and heated under reflux for 16 hours. The solution was filtered and the solvent was evaporated off under reduced pressure to yield a brown solid. The brown solid was recrystallised from a 10% water-propan-1-ol solution to yield α[[(4-methoxyphenyl)methoxy]methyl]-1H-imidazole-1-ethanol as a colourless crystalline solid, having a melting point of 96°–98° C.

(c) 1-(1H-Imidazol-1-yl)-3-[(4-methoxyphenyl)methoxy]-2-propanone

A solution of dry dimethylsulphoxide (18.8 g, 0.24 mol) in dichloromethane (50 ml) was added dropwise over a period of 10 minutes to a stirred solution of oxalyl chloride (14.5 g, 0.11 mol) in dichloromethane (200 ml) at $-60°$ C. The resulting solution was stirred for 2 minutes and then treated with a solution of α[[(4-methoxyphenyl)methoxy]methyl]-1H-imidazole-1-ethanol (24.2 g, 0.092 mol) in dichloromethane (50 ml) and stirred for an additional 15 minutes. Triethylamine (50 g, 0.5 mol) was added to the reaction mixture and the resulting solution was allowed to equilibrate to room temperature. The solution was stirred for 10 minutes, then diluted with dichloromethane (500 ml). The diluted solution was washed with water (3×250 ml), followed by an aqueous saturated solution of ammonium chloride (2×500 ml) and water (500 ml). The solution was dried over sodium sulfate and the solvent was evaporated off under reduced pressure to yield a crude product. The crude product was purified by column chromatography (silica gel, chloroform) to yield 1-(1H-imidazol-1-yl)-3-[4-methoxyphenyl)methoxy]-2-propanone as an orange oil having the following structural characteristics:

$^1$H-NMR (δ-CDCl$_3$): 3.80 (x, 3H), 4.09 (s, 2H), 4.51 (s, 2H), 4.92 (s, 2H), 6.75 (s, 1H), 6.91 and 6.94 (ABq, 2H), 7.08 (s, 1H), 7.27 and 7.31 (ABq, 2H), 7.38 (s, 1H).

(d) Ethyl 4-[3-(1H-imidazol-1-yl)-2-[[(4-methoxyphenyl)methoxy]methyl]-1-propenyl]benzoate A stirred suspension containing [[4-(ethoxycarbonyl)-phenyl]methyl]triphenylphosphonium bromide (11.8 g, 0.0234 mol) in dry tetrahydrofuran (25 ml) at 0° C. under a nitrogen atmosphere was treated with potassium t-butoxide (2.58 g, 0.023 mol). The mixture was allowed to warm up to room temperature and stirred for an additional 90 minutes. The resulting orange mixture was treated with a solution of 1-(1H-imidazol-1-yl)-3-[(4-methoxyphenyl)methoxy]-2-propanone (7.1 g, 0.0273 mol) in dry tetrahydrofuran (25 ml) and stirred for 2 hours. The solvent was evaporated off under reduced pressure and the residue was dissolved in ethyl acetate (300 ml) washed with water (3×150 ml) and extracted into hydrochloric acid (3×200 ml of 5M). The acid solution was basified (K$_2$CO$_3$) and extracted with ethyl acetate (3×250 ml). The extracts were combined, dried over sodium sulfate and the solvent was evaporated off under reduced pressure to yield a crude product. The crude product was purified by column chromatography (silica gel 10% hexane in chloroform). The less polar isomer, ethyl 4-[3-(1H-imidazol-1-yl)-2-[[(4-methoxyphenyl)methoxy]methyl]-1E-propenyl]-benzoate was obtained as a colourless oil having the following structural characteristics:

$^1$H-NMR (δ-CDCl$_3$): 1.40 (t, 3H), 3.80 (s, 3H), 3.88 (s, 2H), 4.39 (q, 2H), 4.41 (s, 2H), 4.76 (s, 2H), 6.80 (s, 1H), 6.85 (s, 1H), 6.89 and 7.25 (ABq, 4H), 7.04 (s, 1H), 7.30 and 8.06 (ABq, 4H) and 7.41 (s, 1H).

Upon further elution of the crude product, the more polar isomer, ethyl 4-[3-(1H-imidazol-1-yl)-2-[[(4-methoxyphenyl)methoxy]methyl]-1Z-propenyl]benzoate was obtained as a colourless oil having the following structural characteristics:

$^1$H-NMR (δ-CDCl$_3$): 1.40 (t, 3H), 3.82 (s, 3H), 3.98 (s, 2H), 4.38 (q, 2H), 4.39 (s, 2H), 4.76 (s, 2H), 6.50 (s, 1H), 6.88 and 7.21 (ABq, 4H), 6.94 (s, 1H), 7.10 (s, 1H), 7.23 and 7.99 (ABq, 4H) and 7.52 (s, 1H).

EXAMPLE 2

4-[3-(1H-Imidazol-1-yl)-2-[[(4-methoxyphenyl)methoxy]methyl]-1E-propenyl]benzoic acid A solution containing ethyl 4-[3-(1H-imidazol-1-yl)-2-[[(4-methoxyphenyl)methoxy]methyl]-1E-propenyl]-benzoate (prepared as in Example 1; 0.7 g, 0.0017 mol) in ethanol (10 ml) was treated with aqueous sodium hydroxide (3.5 ml of 1M). The resulting mixture was stirred at room temperature for 5 hours after which time the solvent was evaporated off under reduced pressure and the resulting residue was dissolved in water (100 ml) and washed with ethyl acetate. The aqueous solution was acidified to pH 6.5 with hydrochloric acid and extracted with ethyl acetate (3×150 ml). The extracts were combined, dried over sodium sulfate, and the solvent was evaporated off under reduced pressure to yield a crude product. The crude product was recrystallised from dichloromethane-pentane to yield 4-[3-(1H-imidazol-1-yl)-2-[[(4-methoxyphenyl)methoxy]methyl]-1E-propenyl]benzoic acid as a colourless, crystalline solid, having a melting point of 120°–122° C. and the following structural characteristics:

Elemental analysis: C, 69.54%; H, 5.94%; N, 7.30%; as against calculated values of C, 69.83%; H, 5.86%; N, 7.40% for C$_{22}$H$_{22}$N$_2$O$_4$.

$^1$H-NMR (δ-CDCl$_3$): 3.80 (s, 3H), 3.89 (s, 2H), 4.42 (s, 2H), 4.81 (s, 2H), 6.83 (s, 1H), 6.87 (s, 1H), 6.90 and 7.25 (ABq, 4H), 7.16 (s, 1H), 7.28 and 8.13 (ABq, 4H) and 7.76 (s, 1H).

EXAMPLE 3

4-[3-(1H-Imidazol-1-yl)-2-[[(4-methoxyphenyl)methoxy]methyl]-1Z-propenyl]benzoic acid Utilizing the procedure described in Example 2 but employing ethyl 4-[3-(1H-imidazol-1-yl)-2-[[(4-methoxyphenyl)methoxy]methyl]-1Z-propenyl] benzoate in lieu of the E isomer, yielded a crude product which was purified by recrystallization from dichloromethane-pentane to yield 4-[3-(1H-Imidazol-1-yl)-2-[[(4-methoxyphenyl)methoxy]methyl]-1Z-propenyl]benzoic acid as a colourless crystalline solid, having a melting point of 123°–125° C. and the following structural characteristics:

Elemental analysis: C, 69.56%; H, 5.88%; N, 7.35%; as against calculated values of: C, 69.83; H, 5.86; N, 7.40% for C$_{22}$H$_{22}$N$_2$O$_4$.

$^1$H-NMR (δCDCl$_3$): 3.77 (s, 3H), 4.01 (s, 2H), 4.37 (s, 2H), 4.79 (s, 2H), 6.56 (s, 1H), 6.87 (part ABq, 2H), 6.96 (s, 1H), 7.11–7.31 (m, 5H), 7.82 (s, 1H), 7.85 (br.s, 1H) and 8.05 (part ABq, 2H).

The Z-geometry of this compound was confirmed by x-ray crystallographic analysis.

EXAMPLE 4

Ethyl 9(1H-imidazol-1-yl)-8-[[4-methoxyphenyl)methoxy]methyl]-7-nonenoate

A stirred suspension containing (7-ethoxy-7-oxoheptyl) triphenylphosphonium bromide (35.5 g. 0.071 mol) in dry tetrahydrofuran (100 ml) was treated with sodium hydride (3.0 g of 60% dispersion in oil, 0.075 mol) and heated under reflux for 2 hours. The resulting red solution was cooled to room temperature and treated with a solution of 1-(1H-imidazol-1-yl)-3-[(4-methoxyphenyl)methoxy]-2-propanone (Example 1c; 10.66 g, 0.041 mol) in dry tetrahydrofuran (50 ml). The solution was stirred for 14 hours at room temperature, diluted with ethyl acetate (500 ml), washed with water (4×100 ml) and extracted with hydrochloric acid (4×250 ml of 1M). The combined acid extracts were washed with ethyl acetate (2×200 ml), basified using sodium bicarbonate and extracted with ethyl acetate (4×200 ml). The extracts were combined, washed with brine, dried over sodium sulfate and the solvent was evaporated off under reduced pressure to yield a crude product. The crude product was purified by column chromatography (silica gel, 20% hexane in chloroform) to yield an isomeric mixture of E- and Z-ethyl 9-(1H-imidazol-1-yl)-8-[[(4-methoxyphenyl)methoxy]methyl]-7-nonenoate as a pale yellow oil having the following structural characteristics:

Elemental analysis: C, 68.61%; H, 7.99%, N, 6.88%; as against calculated values of: C, 68.77; H, 8.05; N, 6.99% for $C_{23}H_{32}N_2O_4$.

$^1$H-NMR ($\delta$-CDCl$_3$): 1.26 (t, 3H), 1.28–1.47 (m, 4H), 1.55–1.69 (m, 2H), 2.06 (t, 2H), 2.29 (t, 2H), 3.81 (s, 3H), 3.86 (s, 2H), 4.13 (q, 2H), 4.37 (s, 2H), 4.54 (s, 2H), 5.52 (t, 1H), 6.84 (s, 1H), 6.89 and 7.24 (ABq, 4H), 7.04 (s, 1H) and 7.42 (s, 1H).

EXAMPLE 5

9-(1H-Imidazol-1-yl)-8-[[(4-methoxyphenyl)methoxy]methyl]-7-nonenoic acid

Utilizing the procedure described in Example 2 employing ethyl 9-(1H-imidazol-1-yl)-8-[[(4-methoxyphenyl)methoxy]methyl-7-nonenoate (as prepared in Example 4) yielded a crude product which was purified by column chromatography (silica gel, 10% ethanol in chloroform) to yield an isomeric mixture of E- and Z-9-(1H-imidazol-1-yl)-8-[[(4-methoxyphenyl)methoxy]methyl]-7-nonenoic acid as a pale yellow oil having the following characteristics:

Elemental analysis: C, 66.85%; H, 7.47%; N, 7.37%; as against calculated values of: C, 66.75%; H, 7.63%; N, 7.41% for $C_{21}H_{28}N_2O_4 + 0.3H_2O$.

$^1$H-NMR ($\delta$-CDCl$_3$): 1.23–1.47 (m, 4H), 1.51–1.70 (m, 2H), 2.07 (t, 2H), 2.33 (t, 2H), 3.82 (s, 3H), 3.87 (s, 2H), 4.36 (s, 2H), 4.55 (s, 2H), 5.05 (br.s, 1H), 5.56 (t, 1H), 6.85 (s, 1H), 6.89 and 7.22 (ABq, 4H), 7.05 (s, 1H) and 7.60 (s, 1H).

EXAMPLE 6

8-(1H-Imidazol-1-yl)-7-[[(4-methoxyphenyl)methoxy]methyl]-6-octenoic acid

A stirred suspension containing 5-(carboxypentyl) triphenylphosphonium bromide (22 g, 0.048 mol) in dry tetrahydrofuran (100 ml) at 0° C. under a nitrogen atmosphere was treated with potassium t-butoxide (11.2 g, 0.10 mol) and stirred for 2 hours at room temperature. The resulting orange mixture was cooled to 0° C. and treated with a solution of 1-(1H-imidazol-1-yl)-3-[(4-methoxyphenyl)methoxy]-2-propanone (as prepared in Example 1c, 6.4 g, 0.025 mol) in dry tetrahydrofuran (25 ml). The reaction mixture was stirred at room temperature for 4 hours after which time the solvent was evaporated off under reduced pressure to yield a residue which was treated with water (200 ml) and extracted with ethyl acetate (4×150 ml). The aqueous solution was acidified to pH 1 using 12M hydrochloric acid washed with ethyl acetate (3×100 ml), basified to pH 5.5 using sodium bicarbonate and extracted with ethyl acetate (4×150 ml). The extracts were combined, washed with water then brine, dried over sodium sulfate and the solvent was evaporated off under reduced pressure to yield a crude product. The crude product was purified by column chromatography (silica gel, 5% ethanol in chloroform) to yield an isomeric mixture of E- and Z-8-(1-H-imidazol-1-yl)-7-[[(4-methoxyphenyl)methoxy]methyl]-6-octenoic acid as a pale yellow oil having the following structural characteristics:

Elemental analysis: C, 65.36%; H, 7.15%; N, 7.57%; as against calculated values of: C, 65.38%; H, 7.41%; N, 7.62% for $C_{20}H_{26}N_2O_4 + 0.5H_2O$ $^1$H-NMR ($\delta$-CDCl$_3$): 1.38–1.54 (m, 2H) 1.54–1.75 (m, 2H), 2.03–2.17 (m, 2H), 2.34 (t, 2H), 3.82 (s, 3H), 3.87 (s, 2H), 4.34 and 4.37 (s, 2H), 4.56 and 4.62 (s, 2H), 5.56 and 5.74 (t, 1H), 6.85 (s, 1H), 6.88 and 7.22 (ABq, 4H), 7.07 (s, 1H), 7.64 (s, 1H) and 10.64 (br.s, 1H, (D$_2$O exchangeable)).

EXAMPLE 7

1-[3-(4-Methoxyphenyl)-2-[[(4-methoxyphenyl)methoxy] methyl]-2-propenyl]-1H-imidazole A stirred suspension containing [(4-methoxyphenyl)methyl]triphenylphosphonium bromide (8.3 g, 0.020 mol) in dry tetrahydrofuran (50 ml) at −20° C. under a nitrogen atmosphere was treated with a solution containing n-butyl lithium (14.3 ml of 1.4M; 0.020 mol) in hexane. The resulting deep-red solution was stirred at −20° C. for 20 minutes and was allowed to warm to room temperature. Stirring was maintained for an additional 20 minutes and the solution was cooled to −20° C. The cooled solution was treated with a solution of 1-(1H-imidazol-1-yl)-3-[(4-methoxyphenyl)methoxy]-2-propanone (Example 1c; 2.6 g, 0.010 mol) in dry tetrahydrofuran (20 ml) and the resulting mixture was stirred at room temperature for 14 hours. Ethyl acetate (500 ml) was added to the mixture and the resulting mixture was washed with water (3×150 ml) and dried over sodium sulfate. The solvent was evaporated off under reduced pressure to yield a crude product which was purified by column chromatography (silica gel, 30% hexane in chloroform) to give an isomeric mixture of E- and Z-1-[3-(4-methoxyphenyl)-2-[[(4-methoxyphenyl)methoxy]methyl]-2-propenyl]-1H-imidazole as a pale-yellow oil having the following structural characteristics:

Elemental analysis: C, 72.16%; H, 6.71%; N, 7.49%; as against calculated values of: C, 72.51%; H, 6.64%; N, 7.69% for $C_{22}H_{24}N_2O_3$.

$^1$H-NMR ($\delta$-CDCl$_3$): 3.82 (s, 6H), 3.87 and 4.01 (s, 2H), 4.37 and 4.41 (s, 2H), 4.72 and 4.80 (s, 2H), 6.51 and 6.77 (s, 1H), 6.81–7.00 (m, 5H), 7.03–7.27 (m, 5H) and 7.44 and 7.50 (s, 1H).

EXAMPLE 8

Ethyl 8-[(1H-imidazol-1-yl)methyl]-11-(4-methoxyphenyl)-7-undecenoate (a) 5-(4-Methoxyphenyl)pent-1-ene A solution containing 4-methoxyphenethyl magnesium iodide (prepared from 60 g, 0.23 mol of 4-methoxyphenethyl iodide and excess magnesium turnings) in anhydrous tetrahydrofuran (200 ml) at 0° C. under a nitrogen atmosphere was treated with 3-bromoprop-1-ene (46.7 g, 0.33 mol) and then stirred at room temperature for 14 hours. The resulting solution was washed with saturated aqueous ammonium chloride solution (3×100 ml) and the aqueous washings were back extracted with dichloromethane (3×100 ml). The tetrahydrofuran and dichloromethane solutions were combined, washed with aqueous sodium thiosulphate solution, dried (MgSO$_4$) and the solvent was evaporated off under reduced pressure to yield an oil which was distilled to yield 5-(4-methoxyphenyl)pent-1-ene as a pale yellow oil (b.p. 65° C., 0.3 mm. Hg) having the following structural characteristics:

$^1$H-NMR ($\delta$-CDCl$_3$): 1.68 (m, 2H), 2.07 (m, 2H), 2.55 (m, 2H), 3.70 (s, 3H), 4.90–5.10 (m, 2H), 5.70–5.90 (m, 1H), 6.81 and 7.06 (ABq, 4H).

(b) [3-(4-Methoxyphenyl)propyl]oxirane 5-(4-Methoxyphenyl)pent-1-ene (18.9 g, 0.107 mol) and 3-chloroperoxybenzoic acid (22.3 g of 85%, 0.11 mol) in dichloromethane (250 ml) was stirred at room temperature for 25 minutes. Dichloromethane (150 ml) was added and the resulting solution was washed with saturated aqueous sodium hydrogen carbonate solution (3×300 ml) and dried (MgSO$_4$). The solvent was evaporated off under reduced pressure to yield an oil which was purified by column chromatography (silica gel, chloroform) to yield [3-(4-methoxyphenyl)propyl]oxirane as a colourless oil having the following structural characteristics:

$^1$H-NMR (δ-CDCl$_3$): 1.40–1.80 (m, 4H), 2.40 (m, 1H), 2.58 (t, 2H), 2.68 (m, 1H), 2.86 (m, 1H), 3.70 (s, 3H), 6.81 and 7.06 (ABq, 4H).

(c) ∝[3-(4-methoxyphenyl)propyl]-1H-imidazole-1-ethanol

Imidazole (20.6 g, 0.303 mol) was added to a solution of [3-(4-methoxyphenyl)propyl]oxirane (19.2 g, 0.101 mol) in acetonitrile (250 ml) and the mixture was heated under reflux for 16 hours. The solvent was evaporated off under reduced pressure to yield a residue which was dissolved in dichloromethane (500 ml), washed with water (3×400 ml) and dried over magnesium sulfate. The solvent was evaporated off under reduced pressure to yield a crude product which was purified by column chromatography (silica gel, 5% ethanol in chloroform) followed by recrystallisation from dichloromethane-pentane to yield ∝[3-(4-methoxyphenyl)propyl]-1H-imidazole-1-ethanol as a colourless crystalline solid, having a melting point of 90.5°–91.5° C., and the following structural characteristics:

$^1$H-NMR (δ-CDCl$_3$): 1.39–1.52 (m, 2H), 1.55–1.94 (m, 2H), 2.56 (t, 2H), 3.74 (s, 3H), 3.64–3.89 (m, 3H), 5.34 (br.s, 1H), 6.78 (s, 1H), 6.80 and 7.08 (ABq, 4H), 6.84 (s, 1H) and 7.24 (s, 1H).

(d) 1-(1H-imidazol-1-yl)-5-(4-methoxyphenyl)-2-pentanone

Utilizing the procedure described in Example 1c and employing ∝[3-(4-methoxyphenyl)propyl]-1H-imidazole-1-ethanol in lieu of ∝[[(4-methoxyphenyl)methoxy]methyl]-1H-imidazole-1-ethanol yielded a crude product which was purified by column chromatography (silica gel, 40% ethyl acetate in hexane to 100% ethyl acetate) to yield 1-(1H-imidazol-1-yl)-5-(4-methoxyphenyl)-2-pentanone as a pale yellow oil having the following structural characteristics:

$^1$H-NMR (δ-CDCl$_3$): 1.81–2.00 (m, 2H), 2.41 (t, 2H), 2.57 (t, 2H), 3.77 (s, 3H), 4.65 (s, 2H), 6.83 and 7.08 (ABq, 4H), 6.85 (s, 1H), 7.09 (s, 1H) and 7.42 (s, 1H).

(e) Ethyl 8-[(1H-imidazol-1-yl)methyl]-11-(4-methoxyphenyl)-7-undecenoate

A stirred suspension containing (7-ethoxy-7-oxoheptyl) triphenylphosphonium bromide (12 g, 0.024 mol) in dry tetrahydrofuran (40 ml) at room temperature under a nitrogen atmosphere was treated with potassium t-butoxide (2.70 g, 0.024 mol). The resulting orange mixture was stirred for 1 hour, treated with a solution of 1-(1H-imidazol-1-yl)-5-(4-methoxyphenyl)-2-pentanone (5.0 g, 0.019 mol) in dry tetrahydrofuran (20 ml) and then stirred for an additional 14 hours. The solvent was evaporated off under reduced pressure and the residue was dissolved in ethyl acetate (300 ml), washed with water (3×150 ml) and extracted into hydrochloric acid (4×150 ml of 5M). The acid extracts were combined, washed with ethyl acetate, basified using sodium carbonate, and extracted with ethyl acetate (4×250 ml). The organic extracts were combined, washed with water then brine, dried over sodium sulfate and the solvent was evaporated off under reduced pressure to yield a crude product. The crude product was purified by column chromatography (silica gel, 40% ethyl acetate in hexane to 100% ethyl acetate) to yield an isomeric mixture of E- and Z-ethyl 8-[(1H-imidazol-1-yl)methyl]-11-(4-methoxyphenyl)-7-undecenoate as a pale-yellow oil having the following structural characteristics:

Elemental analysis: C, 72.22%; H, 8.63%; N, 6.93%; as against calculated values of: C, 72.33%; H, 8.60%; N, 7.03% for C$_{24}$H$_{34}$N$_2$O$_3$.

$^1$H-NMR (δ-CDCl$_3$): 1.26 (t, 3H), 1.26–1.49 (m, 4H), 1.49–1.71 (m, 4H), 1.86–2.09 (m, 3H), 2.10–2.38 (m, 3H), 2.43–2.57 (m, 2H), 3.79 (s, 3H), 4.13 (q, 2H), 4.40 and 4.50 (s, 2H), 5.34 and 5.48 (t, 1H), 6.78–6.89 (m, 3H), 6.99–7.10 (m, 3H) and 7.40 and 7.42 (s, 1H).

EXAMPLE 9

Ethyl 3-[3-(1H-imidazol-1-yl)-2-[[(4-methoxyphenyl)methoxy]methyl]-1-propenyl]benzoate(E- and Z-isomers)

(a) [[3-(Ethoxycarbonyl)phenyl]methyl]triphenylphosphonium bromide

A mixture of 3-(bromoethyl)benzoic acid, ethyl ester (12.2 g, 0.050 mol) and triphenyl phosphine (13.1 g, 0.05 mol) in toluene (50 ml) was stirred at 70° C. for 16 hours to yield [[3-(ethoxycarbonyl)phenyl]methyl]triphenylphosphonium bromide as a colorless crystalline solid which was filtered off, washed with toluene and dried under vacuum.

(b) Ethyl 3-[3-(1H-imidazol-1-yl)-2-[[(4-methoxyphenyl)methoxy]methyl]-1-propenyl]benzoate Utilizing the procedure described in Example 1d but employing [[3-(ethoxycarbonyl)phenyl]methyl]triphenylphosphonium bromide yielded a crude product which was purified by column chromatography (silica gel, ethyl acetate) to initially yield the less polar isomer, ethyl 3-[3-(1H-imidazol-1-yl)-2-[[(4-methoxyphenyl)methoxy)methyl]-1E-propenyl]-benzoate as a pale yellow oil having the following structural characteristics:

Elemental analysis: C, 70.82%; H, 6.45%; N, 6.78%; as against calculated values of: C, 70.92%; H, 6.45%; N, 6.89% for C$_{24}$H$_{26}$N$_2$O$_4$.

$^1$H-NMR (δ-CDCl$_3$): 1.40 (t, 3H), 3.82 (s, 3H), 3.90 (s, 2H), 4.38 (q, 2H), 4.40 (s, 2H), 4.77 (s, 2H), 6.84–6.90 (m, 2H), 6.91 and 7.26 (ABq, 4H), 7.04 (s, 1H), 7.39–7.50 (m, 3H), 7.95 (s, 1H), and 8.00 (d, 1H).

Upon further elution of the crude product, the more polar isomer, ethyl 3-[3-(1H-imidazol-1-yl)-2-[[(4-methoxyphenyl)methoxy]methyl]-1Z-propenyl]benzoate was obtained as a pale yellow oil having the following structural characteristics:

Elemental analysis: C, 70.80%; H, 6.42%; N, 6.84%; as against calculated values of: C, 70.92%; H, 6.45%; N, 6.89% for C$_{24}$H$_{26}$N$_2$O$_4$.

$^1$H-NMR (δ-CDCl$_3$): 1.40 (t, 3H), 3.80 (s, 3H), 4.00 (s, 2H), 4.40 (q, 2H), 4.40 (s, 2H), 4.76 (s, 2H), 6.52 (s, 1H), 6.87 and 7.22 (ABq, 4H), 6.94 (s, 1H), 7.10 (s, 1H), 7.15–7.23 (m, 2H), 7.51 (s, 1H), 7.90 (s, 1H), 7.94 7.99 (m, 1H).

EXAMPLE 10

Ethyl 3-chloro-4-[3-(1H-imidazol-1-yl)-2-[[(4-methoxyphenyl)methoxy]methyl]-1-propenyl]benzoate(E- and Z-isomers)

(a) 2-Chloro-4-methylbenzoic acid

A suspension of 2-chloro-p-xylene (100 ml) in nitric acid (1000 ml of 45%) was heated under reflux for 16 hours. On cooling the mixture was poured into ice water (4000 ml) and the resulting precipitate was filtered off. The crude solid was extracted into 1000 ml of a 1.5M potassium hydroxide solution, filtered and then acidified with hydrochloric acid. The resulting precipitate, which consisted of a mixture of the desired 2-chloro-4-methylbenzoic acid contaminated with 3-chloro-4-methylbenzoic acid, was filtered off and dried under vacuum.

(b) Ethyl 2-chloro-4-methylbenzoate

A mixture of 2-chloro-4-methyl acid and 3-chloro-4-methylbenzoic acid (53 g, 0.312 mol), ethyl iodide (50 ml, 0.624 mol) and potassium carbonate (86.1 g, 0.624 mol) in dimethylformamide (500 ml) was stirred at room temperature for 16 hours. The mixture was diluted with ethyl acetate (1000 ml), washed with water (6×400 ml), dried over sodium sulfate, and the solvent was evaporated off under reduced pressure to yield a mixture of ethyl 2-chloro-4-methylbenzoate and ethyl 3-chloro-4-methylbenzoate. Column chromatography (silica gel, hexane) yielded ethyl 2-chloro-4-methylbenzoate as the more polar of the two isomers having the following structural characteristics:

$^1$H-NMR (δ-CDCl$_3$): 1.40 (t, 3H), 2.32 (s, 3H), 4.39 (q, 2H), 7.07 (d, 1H), 7.12 (s, 1H) and 7.72 (d, 1H).

(c) Ethyl 4-(bromomethyl)-2-chlorobenzoate

A mixture of ethyl 2-chloro-4-methylbenzoate (2.34 g, 0.0118 mol), N-bromosuccinimide (2.05 g, 0.0115 mol), and benzoyl peroxide (0.5 g) in carbon tetrachloride (50 ml) was heated under reflux for 90 minutes. The resulting solution was filtered and the solvent was evaporated off under reduced pressure to yield ethyl 4-(bromomethyl)-2-chlorobenzoate as a yellow crystalline solid having the following structural characteristics:

$^1$H-NMR (δ-CDCl$_3$): 1.39 (t, 3H), 4.39 (q, 4H), 4.41 (s, 2H), 7.28–7.84 (m, 2H) and 8.07 (d, 1H).

(d) [[3-Chloro-4-(ethoxycarbonyl)phenyl]methyl]triphenylphosphonium bromide

Utilizing the procedure described in Example 9a but employing ethyl 4-(bromomethyl)-2-chlorobenzoate in lieu of 3-(bromometyl)benzoic acid, ethyl ester yielded [[3-chloro-4-(ethoxycarbonyl)phenyl]methyl] triphenylphosphonium bromide as a colorless crystalline solid.

(e) Ethyl 3-chloro-4-[3-(1H-imidazol-1-yl)-2-[[(4-methoxyphenyl]methoxy]methyl]-1-propenyl]benzoate Utilizing the procedure described in Example 1d but employing [[3-chloro-4-(ethoxycarbonyl)phenyl]methyl]triphenylphosphonium bromide in lieu of [[4-(ethoxycarbonyl)phenyl]methyl]triphenylphosphonium bromide yielded a crude product which was purified by column chromatography (silica gel, ethyl acetate) to initially yield the less polar isomer, ethyl 3-chloro-4-[3-(1H-imidazol-1-yl)-2-[[(4-methoxyphenyl]methoxy]methyl]-1-E-propenyl]benzoate as a colorless, crystalline solid, having a melting point of 41°–42° C. and the following structural characteristics:

Elemental analysis: C, 65.20%; H, 5.77%; N, 6.16%; as against calculated values of: C, 65.38%, H, 5.71%; N, 6.35% for C$_{24}$H$_{25}$ClN$_2$O$_4$.

$^1$H-NMR (δ-CDCl$_3$): 1.38 (t, 3H), 3.80 (s, 3H), 3.84 (s, 2H), 4.38 (q, 2H), 4.39 (s, 2H), 4.71 (s, 2H), 6.75 (d, 2H), 6.89 and 7.24 (ABq, 4 H), 7.04 (s, 1H), 7.14 (d, 1H), 7.28 (s, 1H), 7.39 (s, 1H) and 7.84 (d, 1H).

Upon further elution of the crude product, more polar isomer, ethyl 3-chloro-4-[3-(1H-imidazol-1-yl)-2-[[(4-methoxyphenyl)methoxy]methyl]-1Z-propenyl]-benzoate was obtained as a pale yellow oil having the following structural characteristics:

Elemental analysis: C, 65.05%; H, 5.82%; N, 6.34% as against calculated values of: C, 65.38%; H, 5.71%; N, 6.35% for C$_{24}$H$_{25}$ClN$_2$O$_4$.

$^1$H-NMR (δ-CDCl$_3$): 1.42 (t, 3H), 3.82 (s, 3H), 3.95 (s, 2H), 4.40 (s, 2H), 4.41 (q, 2H), 4.74 (s, 2H), 6.38 (s, 1H), 6.88 and 7.22 (ABq, 4H), 6.92 (s, 1H), 7.04–7.10 (m, 2H), 7.11 (s, 1H), 7.30 (s, 1H) and 7.76 (d, 1H).

EXAMPLE 11

Ethyl 4-[3-(1H-imdiazol-1-yl)-2-[[(4-methoxyphenyl)methoxy]methyl]-1-propenyl]-3-methoxybenzoate E- and Z isomers)

(a) 2-Methoxy-4-methylbenzoic acid

A stirred mixture of 2-hydroxy-4-methylbenzoic acid (75 g, 0.50 mol), sodium hydroxide (42 g, 1.0 mol) and water (250 ml) was cooled to 10° C. and treated dropwise with dimethyl sulphate (126 g, 1.0 mol). The mixture was stirred for 6 days, poured into water (4000 ml), acidified with sulfuric acid and extracted with dichloromethane (4×600 ml). The extracts were combined, washed with water, dried over sodium sulfate and the solvent was evaporated off under reduced pressure. The resulting oil was treated with aqueous sodium hydroxide (1000 ml of 2M) and heated under reflux for 2 hours. The mixture was acidified with hydrochloric acid and extracted with dichloromethane (3×300 ml). The combined extracts were dried over sodium sulfate and the solvent was evaporated off under reduced pressure to give the crude product as an oil. The crude product was purified by column chromatography (silica gel, chloroform) and recrystallized from chloroform-hexane to yield 2-methoxy-4-methylbenzoic acid as a colorless crystalline solid, having a melting point of 108°–109° C.

(b) Ethyl 2-methoxy-4-methylbenzoate

A stirred solution of 2-methoxy-4-methylbenzoic acid (35 g, 0.211 mol) in benzene (400 ml) was treated dropwise with oxalyl chloride (40 g, 0.317 mol). After 3 hours at room temperature the solvent and excess oxalyl chloride were evaporated under reduced pressure and the resulting crude acid chloride residue was treated with ethanol (200 ml) and heated under reflux for 1 hour. The solvent was evaporated off under reduced pressure to give the crude product which was purified by column chromatography (silica gel, dichloromethane) to yield ethyl 2-methoxy-4-methylbenzoate as a pale yellow oil having the following structural characteristics:

$^1$H-NMR ($\delta$-CDCl$_3$): 1.36 (t, 3H), 2.36 (s, 3H), 3.87 (s, 3H, 4.32 (q, 2H), 6.72–6.80 (m, 2H) and 7.70 (d, 1H).

(c) Ethyl 2-methoxy-4-(bromomethyl)benzoate.

Utilizing the procedure described in Example 10c but employing ethyl 2-methoxy-4-methylbenzoate in lieu of ethyl-2-chloro-4-methylbenzoate yielded a crude product which was purified by column chromatography (silica gel, 50% chloroform in hexane) and recrystallized from ether-pentane to yield ethyl 2-methoxy-4-(bromomethyl)benzoate as a colorless crystalline solid, having a melting point of 70°–71° C.

(d)
[(4-Ethoxycarbonyl-3-methoxyphenyl)methyl]triphenylphosphonium bromide

Utilizing the procedure described in Example 9a but employing ethyl 2-methoxy-4-(bromomethyl)benzoate in lieu of 3-(bromomethyl) benzoic acid yielded [[4-ethoxycarbonyl-3-methoxyphenyl]methyl]triphenylphosphonium bromide as a colorless crystalline solid.

(e) Ethyl 4-[3-(1H-imidazol-1yl)-2-[[(4-methoxyphenyl)methoxy]methyl]-1-propenyl]-3-methoxybenzoate Utilizing the procedure described in Example 1d but employing [(4-ethoxycarbonyl-3-methoxyphenyl)-methyl] triphenylphosphonium bromide in lieu of [[4-(ethoxycarbonyl) phenyl]methyl]triphenylphosphonium bromide yielded a crude product which was purified by column chromatography (silica gel, ethyl acetate) to initially yield the less polar isomer, ethyl 4-[3-(1H-imidazol-1-yl)-2-[[(4-methoxyphenyl)methoxy]methyl]-1E-propenyl]-3-methoxybenzoate as a pale yellow oil having the following structural characteristics:

Elemental analysis: C, 68.42%; H, 6.41%; N, 6.26%; as against calculated values of: C, 68.79%; H, 6.47%; N, 6.42% for C$_{25}$H$_{28}$N$_2$O$_5$.

$^1$H-NMR ($\delta$-CDCl$_3$): 1.39 (t, 3H), 3.82 (s, 3H), 3.88 (s, 3H), 3.90 (s, 2H), 4.36 (q, 2H), 4.44 (s, 2H), 4.76 (s, 2H), 6.80–6.98 (m, 4H), 6.92 and 7.27 (ABq, 4H), 7.06 (s, 1H) and 7.83 (d, 1H).

Upon further elution of the crude product, the more polar isomer, ethyl 4-[3-(1H-imidazol-1-yl)-2-[[(4-methoxyphenyl) methoxy]methyl]-1Z-propenyl]-3-methoxybenzoate was obtained as a colorless crystalline solid, having a melting point of 74.0°–74.5° C. (dichloromethane-hexane) and the following structural characteristics:

Elemental analysis: C, 68.37%; H, 6.47%; N, 6.38%; as against calculated values of: C, 68.79%; H, 6.47%; N, 6.42% for C$_{25}$H$_{28}$N$_2$O$_5$.

$^1$H-NMR ($\delta$-CDCl$_3$): 1.40 (t, 3H), 3.82 (s, 3H), 3.85 (s, 3H), 4.00 (s, 2H), 4.37 (q, 2H), 4.39 (s, 2H), 4.76 (s, 2H), 6.46 (s, 1H), 6.77–6.83 (m, 2H), 6.88 and 7.22 (ABq, 4H), 6.95 (s, 1H), 7.05 (s, 1H), 7.52 (s, 1H) and 7.75 (d, 1H).

EXAMPLE 12

Ethyl 4-[2-(1H-imidazol-1-ylmethyl)-5-(4-methoxyphenyl)-1-pentenyl]benzoate-(E- and Z-isomers)

A stirred solution of potassium t-butoxide (5.0 g, 0.045 mol) in dry dimethylformamide (20 ml) at room temperature under a nitrogen atmosphere was treated with [[4-(ethoxycarbonyl)phenyl]methyl]triphenylphosphonium bromide (20.0 g, 0.0396 mol) in portions over 5 minutes. The resulting red suspension was stirred for 5 minutes and then treated dropwise with a solution of 1-(1H-imidazol-1-yl)-5-(4-methoxyphenyl)-2-pentanone (Example 8d; 4.0 g, 0.0155 mol) in dry dimethylformamidie (4 ml) over 5 minutes. The mixture was then heated at 120° C. for 1 hour. On cooling the reaction mixture was poured onto ice water (200 ml) and extracted with ethyl acetate (2×50 ml). The extracts were combined, washed with water, dried over magnesium sulfate and the solvent was evaporated off under reduced pressure to give the crude product. The crude product was purified by column chromatography (silica gel, 5% methanol in dichloromethane) to initially yield the less polar isomer, ethyl 4-[2-(1H-imidazol-1-ylmethyl)-5-(4-methoxyphenyl)-1Z-pentenyl]benzoate as a pale yellow oil having the following structural chracteristics:

$^1$H-NMR ($\delta$-CDCl$_3$): 1.41 (t, 3H), 1.78 (m, 2H), 2.08 (t, 2H), 2.58 (t, 2H), 3.80 (s, 3H), 4.39 (q, 2H), 4.66 (s, 2H), 6.66 (s, 1H), 6.81 and 7.26 (ABq, 4H), 6.86 (S, 1H), 7.10 (s, 1H), 7.22 (s, 1H), 7.15 and 8.05 (ABq, 4H).

Upon further elution of the crude product the more polar isomer, ethyl 4-[2-[(1H-imidazol-1-yl)-methyl]-5-(4-methoxyphenyl)-1E-pentenyl]benzoate was obtained as a colorless crystalline solid, having a melting point of 92°–94° C. (ether-hexane) and the following structural characteristics:

Elemental analysis: C, 74.43%; H, 7.02%; N, 6.91%; as against calculated values of: C, 74.23%; H, 6.98%; N, 6.93% for C$_{25}$H$_{28}$N$_2$O$_3$.

$^1$H-NMR ($\delta$-CDCl$_3$): 1.40 (t, 3H), 1.60–1.84 (m, 2H), 2.12–2.26 (m, 2H), 2.52 (t, 2H), 3.80 (s, 3H), 4.39 (q, 2H), 4.62 (s, 2H), 6.31 (s, 1H), 6.81 and 7.20 (ABq, 4H), 6.91 (s, 1H), 7.10 (s, 1H), 7.16 and 7.94 (ABq, 4H) and 7.31 (s, 1H).

EXAMPLE 13

Ethyl 4-[2-[[(4-fluorophenyl)methoxy]methyl]-3-(1H-imidazol-1-yl)-1-propenyl]benzoate (E and Z-isomers)

(a) 2,3-Epoxypropyl-4-fluorobenzylether

Utilizing the procedure described in Example 1a but employing 4-fluorobenzyl alcohol in lieu of 4-methoxybenzyl alcohol yielded 2,3-epoxypropyl-4-fluorobenzylether as a pale yellow oil having the following structural characteristics:

$^1$H-NMR ($\delta$-CDCl$_3$): 2.62 (m, 1H), 2.81 (t, 1H), 3.20 (m, 1H), 3.43 (dd, 1H), 3.80 (dd, 1H), 4.57 (q, 2H) and 7.20 and 7.34 (ABq, 4H).

(b)
$\alpha$ [[(4-fluorophenyl)methoxy]methyl]-1H-imidazole-1-ethanol

A mixture of 2,3-epoxypropyl-4-fluorobenzyl ether (29 g, 0.159 mol) of imidazole (33.5 g, 0.5 mol) in acetonitrile (250 ml) was heated under reflux for 6 hours. The solvent was evaporated off under reduced pressure and the residue was dissolved in ethyl acetate (300 ml) and washed with water (5×100 ml). The resulting solution was extracted with hydrochloric acid (3×100 ml; 5M) and the acid extracts were combined and washed with ethyl acetate (2×100 ml). The acid solution was basified (NaHCO$_3$) and extracted with ethyl acetate (3×100 ml). The extracts were combined, washed (brine), dried (MgSO$_4$) and the solvent was evaporated off under reduced pressure to yield a crude product. The crude product was purified by column chromatography (silica gel, 5% methanol in dichloromethane) to yield α-[[(4-fluorophenyl)methoxy]methyl]-1H-imidazole-1-ethanol as a pale yellow oil having the following structural characteristics:

Elemental analysis: C, 62.02%; H, 6.10%; N, 11.13%; as against calculated values of: C, 62.39%; H, 6.04%; N, 11.19% for $C_{13}H_{15}FN_2O_2$.

$^1$H-NMR (δ-CDCl$_3$): 3.37–3.52 (m, 2H), 3.89–4.14 (m, 3H), 4.50 (s, 2H), 6.88 (d, 2H), 7.00–7.10 (m, 2H) and 7.25–7.38 (m, 3H).

(c) 3-[(4-Fluorophenyl)methoxy]-1-(1H-imidazol-1-yl)-2-propanone

Utilizing the procedure described in Example 1c but employing α-[[(4-fluorophenyl)methoxy]methyl]-1H-imidazole-1-ethanol in lieu of α-[[(4-methoxyphenyl)methoxy]methyl]-1H-imidazole-1-ethanol yielded 3-[(4-fluorophenyl)methoxy]-1-(1H-imidazol-1-yl)-2-propane as a yellow oil having the following structural characteristics:

$^1$H-NMR (δ-CDCl$_3$): 4.10 (s, 2H), 4.61 (s, 2H), 4.98 (s, 2H), 6.84 (s, 1H), 6.98–7.16 (m, 3H) and 7.28–7.44 (m, 3H).

(d) Ethyl 4-[2-[[(4-fluorophenyl)methoxy]methyl]-3-(1H-imidazol-1-yl)-1-propenyl]benzoate (E and Z isomers)

Utilizing the procedure described in Example 1d but employing 1-[3-[(4-fluorophenyl)methoxy]-1-(1H-imidazol-1-yl)-2-propanone yielded a crude product which was purified by column chromatography (silica gel, ethyl acetate) to initially yield the less polar isomer, ethyl 4-[2-[[(4-fluorophenyl)methoxy]methyl]-3-(1H-imidazol-1-yl)-1E-propenyl]benzoate as a pale yellow oil having the following structural characteristics:

$^1$H-NMR (δ-CDCl$_3$): 1.41 (t, 3H), 3.91 (s, 2H), 4.40 (q, 2H), 4.45 (s, 2H), 4.80 (s, 2H), 6.84 (s, 1H), 6.91 (s, 1H), 6.95–7.80 (m, 8H) and 7.09 (q, 2H).

Upon further elution of; the crude product, the more polar isomer, ethyl 4-[2-[[(4-fluorophenyl)methoxy]-methyl]-3-(1H-imidazol-1-yl)-1Z-propenyl]benzoate was obtained as a pale yellow oil having the following structural characteristics:

Elemental analysis: C, 69.95%; H, 6.05%; N, 6.76%; as against calculated values of: C, 70.03%; H, 5.88%; N, 7.10% for $C_{23}H_{23}FN_2O_3$.

$^1$H-NMR (δ-CDCl$_3$): 1.42 (t, 3H), 4.02 (s, 2H), 4.41 (q, 2H), 4.42 (s, 2H), 4.80 (s, 2H), 6.55 (s, 1H), 6.97 (s, 1H), 6.95–7.12 (m, 2H), 7.10 (s, 1H), 7.21 and 8.00 (ABq, 4H), 7.16–7.40 (m, 2H), and 7.54 (s, 1H).

EXAMPLE 14

Ethyl 4-[6,6-dimethyl-2-(1H-imidazol-1-ylmethyl)-1-heptenyl]benzoate (E- and Z-isomers)

(a) 6,6-Dimethyl-1-heptene

A solution of 2,2-Dimethylpropane (15.1 g, 0.10 mol) in dry tetrahydrofuran (80 ml) was added dropwise to a mixture of magnesium turnings (2.43 g, 0.10 mol) in dry tetrahydrofuran (20 ml) containing a single crystal of iodine, at such a rate so as to maintain the solvent at reflux. The resulting solution was allowed to cool to room temperature and decanted from the residual magnesium under nitrogen into a fresh flask. The solution was diluted with dry tetrahydrofuran (150 ml), cooled to −20° C. under an atmosphere of nitrogen treated with cuprous bromide dimethyl sulphide complex and stirred for 20 minutes. The resulting solution was then treated with 4-bromo-1-butene (13.5 g, 0.10 mol) and stirred at −20° C. for 16 hours and then at 20° C. for 4 hours. The reaction mixture as quenched with saturated aqueous ammonium chloride solution (10 ml), diluted with ether (200 ml) and washed with an aqueous solution of ammonia (2×200 ml of 10%). The solution was dried over sodium sulfate and distilled at atmospheric pressure to yield 6,6-dimethyl-1-heptene as a colourless oil, having a boiling point of 120°–125° C., and the following structural characteristics:

$^1$H-NMR (δ-CDCl$_3$): 0.86 (s, 9H), 1.12–1.22 (m, 2H), 1.24–1.44 (m, 2H), 2.03 (q, 2H), 4.91–5.08 (m, 2H), and 5.76–5.94 (m, 1H).

(b) (4,4-Dimethylpentyl)oxirane

A solution of 6,6-dimethyl-1-heptene (5.33 g, 0.0423 mol) and m-chloroperoxybenzoic acid (9.5 g of 85%, 0.048 mol) in dichloromethane (100 ml) was stirred at room temperature for 16 hours. The resulting solution was washed and aqueous sodium hydroxide (3×50 ml of 2M) and dried over sodium sulfate. The solvent was distilled off at atmospheric pressure to yield (4,4-dimethylpentyl)oxirane as a residue, having the following structural characteristics:

$^1$H-NMR (δ-CDCl$_3$): 0.87 (s, 9HG), 1.12–1.60 (m, 6H), 2.46–2.52 (m, 1H), 2.76 (t, 1H), and 2.88–2.98 (m, 1H).

(c) α-(4,4-dimethylpentyl)-1H-imidazole-1-ethanol

Utilizing the procedure described in Example 8c and employing (4,4-dimethylpentyl)oxirane in lieu of [3-(4-methoxyphenyl)propyl]oxirane yielded a crude product which was purified by column chromatography (silica gel, chloroform) to yield α-(4,4-dimethylpentyl)-1H-imidazole-1-ethanol as a pale yellow oil having the following structural characteristics:

Elemental analysis: C, 65.70%; H, 10.23%; N, 12.48%; as against calculated values of C, 65.72%; H, 10.57%; N, 12.77% for $C_{12}H_{22}N_2O \cdot 0.5H_2O$.

$^1$H-NMR (δCDCl$_3$: 0.88 (s, 9H), 1.10–1.62 (m, 6H, 1.50 (broad s, 1H), 3.76–4.20 (m, 3H), 6.92 (s, 2H), and 7.38 (s, 1H).

(d) 6,6-Dimethyl-1-(1H-imidazol-1-yl)-2-heptanone

Utilising the procedure described in Example 1c and employing α-(4,4-dimethylpentyl)-1H-imidazole-1-ethanol in lieu of α-[[(4-methoxyphenyl)methoxy]methyl]-1H-imidazole-1-ethanol yielded a crude product which was purified by column chromatography (silica gel, chloroform) to yield 6,6-dimethyl-1-(1H-imidazol-1-yl)-2-heptanone as a colourless crystalline solid, having a melting point of 45°–46° C. (ether-hexane) and the following structural characteristics:

Elemental analysis: C, 67.46%; H, 9.6%, N, 13.12%; as against calculated values of C, 67.44%; H, 9.72%; N, 13.11%; for $C_{12}H_{20}N_2O \cdot 0.3H_2O$.

$^1$H-NMR ($\delta$-CDCl$_3$): 0.88 (s, 9H), 1.10–1.24 (m, 2H), 1.52–1.68 (m, 2H), 2.43 (t, 2H), 4.77 (s, 2H), 6.90 (s, 1H), 7.11 (s, 1H), and 7.47 (s, 1H).

(e) Ethyl 4-[6,6-dimethyl-2-(1H-imidazol-1-ylmethyl)-1-heptenyl]benzoate E- and Z-isomers Utilising the procedure described in Example 12 and employing 6,6-dimethyl-1-(1H-imidazol-1-yl)-2-heptanone in lieu of 1-(1H-imidazol-1-yl)-5-(4-methoxyphenyl)-2-pentanone yielded a crude product which was purified by column chromatography (silica gel, chloroform) to initially yield the less polar isomer, ethyl 4-[6,6-dimethyl-2-(1H-imidazol-1-ylmethyl)-1Z-heptenyl]benzoate as a pale yellow oil having the following structural characteristics:

Elemental analysis: C, 74.11%; H, 8.57%; N, 7.84%; as against calculated values of C, 74.16%; H, 8.54%; N, 7.86% for $C_{22}H_{30}N_2O_2 \cdot 0.1H_2O$.

Elemental analysis: C, 74.11%; H, 8.57%; N, 7.84%; as against calculated values of C, 74.16%; H, 8.54%; N, 7.86% for $C_{22}H_{30}N_2O_3 \cdot 0.1H_2O$.

$^1$H-NMR ($\delta$-CDCl$_3$): 0.87 (s, 9H), 1.10–1.24 (m, 2H), 1.34–1.52 (m, 2H), 1.40 (t, 3H), 2.00 (t, 2H), 4.40 (q, 2H), 4.68 (s, 2H), 6.67 (s, 1H), 6.82 (d, 1H), 7.06 (d, 1H), 7.28 and 8.05 (ABq, 4H) and 7.44 (s, 1H).

Upon further elution of the crude product, the more polar isomer, ethyl 4-[6,6-dimethyl-2-(1H-imidazol-1-ylmethyl)-1E-heptenyl]benzoate was obtained as a pale yellow oil having the following structural characteristics:

$^1$H-NMR ($\delta$-CDCl$_3$): 0.87 (s, 9H), 1.10–1.20 (m, 2H), 1.30–1.48 (m, 2H), 1.40 (t, 3H), 2.13 (t, 2H), 4.39 (q, 2H), 4.66 (s, 2H), 6.32 (s, 1H), 6.97 (d, 1H), 7.12 (d, 1H), 7.25 and 8.02 (ABq, 4H) and 7.55 (s, 1H).

EXAMPLE 15

Ethyl 4-[5-[4-[(1,1-dimethylethoxy)carbonyl]phenyl]-2-(1H-imidazol-1-ylmethyl)-1-pentenyl]benzoate (E- and Z-isomers)

(a) 4-(4-Pentenyl)benzoic acid n-Butyl lithium (100 ml of 2.5M solution in hexane, 0.25 mol) was added to a stirred solution of diisopropylamine (35 ml, 0.25 mol) in dry tetrahydrofuran (250 ml) at −78° C. under a nitrogen atmosphere. The solution was allowed to warm up to −5° C., stirred for 30 minutes, cooled back to −78° C., and treated with p-toluic acid (17.0 g, 0.125 mol) in portions over 2 hours. The resulting mixture was allowed to warm up to −5° C. and stirred for 30 minutes. The resulting black solution was again cooled to −78° C. and treated dropwise with a solution of 4-bromobutene (17 ml, 0.166 mol) in dry tetrahydrofuran (100 ml) over 1 hour. The resulting yellow solution was allowed to warm up to room temperature and stirred for an additional 12 hours. The solvent was evaporated off under reduced pressure and the residue was treated with hydrochloric acid (500 ml of 5M) and extracted with dichloromethane (3×300 ml). The combined extracts were washed with water (2×250 ml), brine (250 ml) and dried over sodium sulfate. The solvent was evaporated off under reduced pressure to give crude 4-(4-pentenyl)benzoic acid as a solid.

(b) 1,1-Dimethylethyl 4-(4-pentenyl)benzoate

A solution of 4-(4-pentenyl)benzoic acid (42 g, 0.22 mol) in benzene (250 ml) was added dropwise to a solution of oxalyl chloride (60 ml) in benzene (200 ml) over 1 hour. The solution was stirred for 1 hour at room temperature and then heated under reflux for 2 hours. The solvent and excess oxalyl chloride was evaporated off under reduced pressure to give an oily residue which was dissolved in dry tetrahydrofuran (250 ml) and added dropwise over 1 hour to a stirred solution of lithium t-butoxide [prepared from t-butanol (21 g, 0.283 mol) in dry tetrahydrofuran (200 ml) at −20° C. and n-butyl lithium (114 ml of 2.5M solution in hexane, 0.285 mol)]. The resulting mixture was allowed to warm up to room temperature and stirred for an additional 12 hours. The solvent was evaporated off under reduced pressure and the residue was treated with water (500 ml) and extracted with chloroform (3×500 ml). The combined extracts were dried over sodium sulfate and the solvent was evaporated off under reduced pressure to yield crude 1,1-dimethylethyl 4-(4-pentenyl)benzoate as an oil.

(c) 1,1-Dimethylethyl 4-(3-oxiranylpropyl)benzoate

Utilizing the procedure described in Example 8b and employing 1,1-dimethylethyl 4-(4-penteyl)benzoate in lieu of 5-(4-methoxyphenyl)pent-1-ene yielded a crude product which was purified by column chromatography (silica gel, 30% hexane in chloroform) to yield 1,1-dimethylethyl 4-(3-oxiranylpropyl)benzoate as a pale yellow oil having the following structural characteristics:

$^1$H-NMR ($\delta$-CDCl$_3$): 1.59 (s, 9H), 1.70–1.82 (m, 4H), 2.44–2.50 (m, 1H), 2.70–2.80 (m, 1H), 2.74 (t, 2H), 2.90–2.98 (m, 1H), 7.23 and 7.93 (ABq, 4H).

(d) 1,1-Dimethylethyl 4-[1-[4-hydroxy-5-(1H-imidazol-1-yl)pentyl]benzoate

Utilizing the procedure described in Example 8c but employing 1,1-dimethylethyl 4-(3-oxiranylpropyl)benzoate in lieu of [3-(4-methoxyphenyl)propyl]oxirane yielded a crude product which was purified by column chromatography (silica gel, 5% ethanol in chloroform) to yield 1,1-dimethylethyl 4-[1-[4-hydroxy-5-(1H-imidazol-1-yl)pentyl]]benzoate as a colorless crystalline solid having a melting point of 78°–80° C., and the following structural characteristics:

Elemental analysis: C, 68.93%; H, 7.94%; N, 8.37%; as against calculated values of C, 69.07%; H, 7.93%; N, 8.48% for $C_{19}H_{26}N_2O_3$.

$^1$H-NMR ($\delta$-CDCl$_3$): 1.42–1.60 (m, 2H), 1.58 (s, 9H), 1.63–2.04 (m, 2H), 2.70 (t, 2H), 3.70–3.98 (m, 3H), 4.40 (broad s, 1H), 6.83 (d, 1H), 6.85 (d, 1H), 7.22 and 7.90 (ABq, 4H), and 7.29 (s, 1H).

(e) 1,1-Dimethylethyl-4-[1-[5-(1H-imidazol-1-yl)-4-oxopentyl]]benzoate

Utilizing the procedure described in Example 1c and employing 1,1-dimethylethyl-4-[1-[4-hydroxy-5-(1H-imidazol-1-yl)pentyl]]benzoate in lieu of α-[[(4-methoxyphenyl)methoxy]methyl]-1H-imidazole-1-ethanol yielded a crude product which was purified by column chromatography (silica gel, 5% ethanol in chloroform)

to yield 1,1-dimethylethyl-4-[1-[5-(1H-imidazol-1-yl)-4-oxopentyl]]benzoate as a colorless crystalline solid having a melting point of 66°–69° C. (ether) and the following structural characteristics:

Elemental analysis: C, 69.66%; H, 7.42%; N, 8.41%; as against calculated values of C, 69.49%; H, 7.37%; N, 8.53% for $C_{19}H_{24}N_2O_3$.

$^1$H-NMR ($\delta$-CDCl$_3$): 1.59 (s, 9H), 1.96 (t, 2H), 2.42 (t, 2H), 2.67 (t, 2H), 4.68 (s, 2H), 6.85 (s, 1H), 7.11 (s, 1H), 7.20 and 7.92 (ABq, 4H), and 7.43 (s, 1H).

(f) Ethyl 4-[5-[4-[(1,1-dimethylethoxy)carbonyl]phenyl]-2-(1H-imidazol-1-ylmethyl)-1-pentenyl]benzoate Utilizing the procedure described in Example 12 and employing 1,1-dimethylethyl-4-[1-[5-(1H-imidazol-1-yl)-4-oxopentyl]]benzoate in lieu of 1-(1H-imidazol-1-yl)-5-(4-methoxyphenyl)-2-pentanone yielded a crude product which was purified by column chromatography (silica gel, chloroform) to initially yield the less polar isomer, ethyl 4-[5-[4-[(1,1-dimethylethoxy)carbonyl]phenyl]-2-(1H-imidazol-1-ylmethyl)-1Z-pentenyl]benzoate as a colorless oil having the following structural characteristics:

$^1$H-NMR ($\delta$-CDCl$_3$): 1.42 (t, 3H), 1.61 (s, 9H), 1.60–1.84 (m, 2H), 2.02–2.14 (m, 2H), 2.60 (t, 2H), 4.39 (q, 2H), 4.62 (s, 2H), 6.66 (s, 1H), 6.80 (s, 1H), 7.06 and 7.30 (m, 5H), 7.23 (s, 1H), 7.89 (d, 2H), and 8.06 (d, 2H).

Upon further elution of the crude product, the more polar isomer, ethyl 4-[5-[4-[(1,1-dimethylethoxy)carbonyl]phenyl]-2-(1H-imidazol-1-ylmethyl)-1E-pentenyl]benzoate as a colorless oil having the following structural characteristics:

$^1$H-NMR ($\delta$-CDCl$_3$): 1.41 (t, 3H), 1.61 (s, 9H), 1.66–1.84 (m, 2H), 2.18–2.28 (m, 2H), 2.62 (t, 2H), 4.40 (q, 2H), 4.64 (s, 2H), 6.36 (s, 1H), 6.92 (s, 1H), 7.11 (s, 1H), 7.14 and 7.90 (ABq, 4H), 7.21 and 8.00 (ABq, 4H), and 7.53 (s, 1H).

EXAMPLE 16

4-[6,6-Dimethyl-2-(1H-imidazol-1-ylmethyl)1E-heptenyl]benzoic acid

A solution containing ethyl 4-[6,6-dimethyl-2-(1H-imidazol-1-ylmethyl)-1-heptenyl]benzoate (prepared as in Example 14; 0.7 g, 0.0017 mol) in ethanol (10 ml) was treated with aqueous sodium hydroxide (3.5 ml of 1M). The resulting mixture was stirred at room temperature for 5 hours after which time the solvent was evaporated off under reduced pressure and the resulting residue was dissolved in water (100 ml) and washed with ethyl acetate. The aqueous solution was acidified to pH 6.5 with hydrochloric acid and extracted with ethyl acetate (3×150 ml). The extracts were combined, dried over sodium sulfate, and the solvent was evaporated off under reduced pressure to yield a crude product. The crude product was recrystallised from dichloromethane-pentane to yield 4-[6,6-dimethyl-2-(1H-imidazol-1-ylmethyl)-1E-heptenyl]benzoic acid as a colorless, crystalline solid, having a melting point of 190°–192° C. and the following structural characteristics:

Elemental analysis: C, 73.17%, H, 8.07%; N, 8.52%; as against calculated values of C, 73.59%; H, 8.03%; N, 8.58% for $C_{20}H_{26}N_2O_2$.

'H-NMR ($\delta$-CDCl$_3$): 0.85 (s, 9H), 1.05–1.20 (m, 2H), 1.30–1.50 (m, 2H), 2.08–2.20 (t, 2H), 4.68 (s, 2H), 6.37 (s, 1H), 6.99 (s, 1H), 7.21 (s, 1H), 7.28 and 8.08 (AB$_q$, 4H), 7.83 (s, 1H), and 8.15 (broad s, 1H).

EXAMPLE 17

Ethyl 4-[5-(4-carboxyphenyl)-2-(1H-imidazol-1-ylmethyl)-1E-pentenyl]benzoate

A solution containing ethyl 4-[5-[4-[(1,1-dimethylethoxy)carbonyl]phenyl]-2-(1H-imidazol-1-ylmethyl)-1E-pentenyl]benzoate (prepared as in Example 15; 3.5 g, 0.0074 mol) in acetic acid (45 ml) was treated with aqueous hydrochloric acid (5% of 35.4%). The solution was stirred at room temperature for three hours after which time the solution was basified with sodium hydrogen carbonate, diluted with water (500 ml) and extracted with dichloromethane (4×300 ml). The extracts were combined, dried over sodium sulphate, and the solvent was evaporated off under reduced pressure to yield a crude product. The crude product was purified by column chromatography (silica gel, 10% ethanol in chloroform) to yield ethyl 4-[5-(4-carboxyphenyl)-2-(1H-imidazol-1-ylmethyl)1E-pentenyl]benzoate as a colorless crystalline solid having a melting point of 167°–170° C. (chloroform/benzene) and the following structural characteristics:

Elemental analysis: C, 71.33%; H, 6.22%; N, 6.50%; as against calculated values of C, 71.75%; H, 6.26%; N, 6.69% for $C_{25}H_{26}N_2O_4$.

'H-NMR ($\delta$-CDCl$_3$): 1.40 (t, 3H), 1.60–1.85 (m, 2H), 2.09–2.20 (m, 2H), 2.62 (t, 2H), 4.38 (q, 2H), 4.62 (s, 2H), 6.44 (s, 1H), 6.91 (s, 1H), 7.03 (broad s, 1H), 7.10–7.30 (m, 5H), 7.67 (s, 1H), 7.99 (d, 2H), and 8.02 (d, 2H).

Table I represents the compounds prepared in the preceding examples.

TABLE I

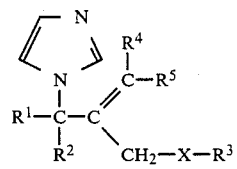

| COMPOUND OF EXAMPLE NO. | R$^1$ | R$^2$ | R$^3$ | R$^4$ | R$^5$ | X |
|---|---|---|---|---|---|---|
| 1 | —H | —H | 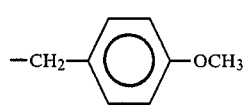 | —H | 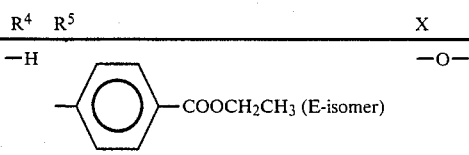 | —O— |

TABLE I-continued

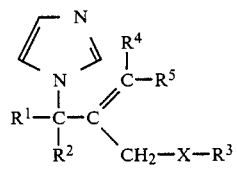

| Compound of Example No. | R¹ | R² | R³ | R⁴ | R⁵ | X |
|---|---|---|---|---|---|---|
| 1 | —H | —H | —CH₂—C₆H₄—OCH₃ | —H | —C₆H₄—COOCH₂CH₃ (Z-isomer) | —O— |
| 2 | —H | —H | —CH₂—C₆H₄—OCH₃ | —H | —C₆H₄—COOH (E-Isomer) | —O— |
| 3 | —H | —H | —CH₂—C₆H₄—OCH₃ | —H | —C₆H₄—COOH (Z-Isomer) | —O— |
| 4 | —H | —H | —CH₂—C₆H₄—OCH₃ | —H | —(CH₂)₅COOCH₂CH₃ (E & Z isomers) | —O— |
| 5 | —H | —H | —CH₂—C₆H₄—OCH₃ | —H | —(CH₂)₅COOH (E & Z isomers) | —O— |
| 6 | —H | —H | —CH₂—C₆H₄—OCH₃ | —H | —(CH₂)₄COOH (E & Z isomers) | —O— |
| 7 | —H | —H | —CH₂—C₆H₄—OCH₃ | —H | —C₆H₄—OCH₃ (E & Z isomers) | —O— |
| 8 | —H | —H | —CH₂—C₆H₄—OCH₃ | —H | —(CH₂)₅COOCH₂CH₃ (E & Z isomers) | —CH₂— |
| 9 | —H | —H | —CH₂—C₆H₄—OCH₃ | —H | —C₆H₄—COOCH₂CH₃ (E-isomer) | —O— |
| 9 | —H | —H | —CH₂—C₆H₄—OCH₃ | —H | —C₆H₄—COOCH₂CH₃ (Z-isomer) | —O— |
| 10 | —H | —H | —CH₂—C₆H₄—OCH₃ | —H | 2-Cl-C₆H₃—COOCH₂CH₃ (E-isomer) | —O— |

TABLE I-continued

[Structure: pyrazole/imidazole ring attached to C(R¹)(R²)–C(=C(R⁴)(R⁵))–CH₂–X–R³]

| COMPOUND OF EXAMPLE NO. | R¹ | R² | R³ | R⁴ | R⁵ | X |
|---|---|---|---|---|---|---|
| 10 | –H | –H | –CH₂–C₆H₄–OCH₃ | –H | 2-Cl-C₆H₃-COOCH₂CH₃ (Z-isomer) | –O– |
| 11 | –H | –H | –CH₂–C₆H₄–OCH₃ | –H | 2-OCH₃-C₆H₃-COOCH₂CH₃ (E-isomer) | –O– |
| 11 | –H | –H | –CH₂–C₆H₄–OCH₃ | –H | 2-OCH₃-C₆H₃-COOCH₂CH₃ (Z-isomer) | –O– |
| 12 | –H | –H | –CH₂–C₆H₄–OCH₃ | –H | C₆H₄–COOCH₂CH₃ (Z-isomer) | –CH₂– |
| 12 | –H | –H | –CH₂–C₆H₄–OCH₃ | –H | C₆H₄–COOCH₂CH₃ (E-isomer) | –CH₂– |
| 13 | –H | –H | –CH₂–C₆H₄–F | –H | C₆H₄–COOCH₂CH₃ (E-isomer) | –O– |
| 13 | –H | –H | –CH₂–C₆H₄–F | –H | C₆H₄–COOCH₂CH₃ (Z-isomer) | –O– |
| 14 | –H | –H | –CH₂–C(CH₃)₃ | –H | C₆H₄–COOCH₂CH₃ (E-isomer) | –CH₂– |
| 14 | –H | –H | –CH₂–C(CH₃)₃ | –H | C₆H₄–COOCH₂CH₃ (Z-isomer) | –CH₂– |
| 15 | –H | –H | –CH₂–C₆H₄–COOC(CH₃)₃ | –H | C₆H₄–COOCH₂CH₃ (E-isomer) | –CH₂– |
| 15 | –H | –H | –CH₂–C₆H₄–COOC(CH₃)₃ | –H | C₆H₄–COOCH₂CH₃ (Z-isomer) | –CH₂– |

TABLE I-continued

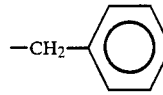

| COMPOUND OF EXAMPLE NO. | R¹ | R² | R³ | R⁴ | R⁵ | X |
|---|---|---|---|---|---|---|
| 16 | —H | —H | —CH₂—C(CH₃)₃ | —H | —⟨phenyl⟩—COOH (E-isomer) | —CH₂— |
| 17 | —H— | —H— | —CH₂—⟨phenyl⟩—COOH | —H | —⟨phenyl⟩—COOCH₂CH₃ (E-isomer) | —CH₂— |

Various compounds of the present invention were evaluated utilizing an in vitro radioimmunoassay as described in the following Example in order to determine inhibition of thromboxane production.

EXAMPLE 18

Thromboxane production in Human Platelet Rich Plasma (a) Platelet rich plasma (prp) preparation Human venous blood was collected from healthy male donors, who had denied any medication during the previous 14 days. Nine volumes of blood were mixed with one volume of 3.24% trisodium citrate. The citrated blood was centrifuged at 160 g for 10 mins. at 22° C. to obtain platelet rich plasma (prp). The platelets were then counted on a Coulter counter, and the platelet count was adjusted to 200,000 per µl with plasma.

(b) Thromboxane generation

The prp was then dispensed as aliquots into micro-Eppendorf tubes, maintained at 37° C. in a dry bath. The compound to be evaluated was dissolved either in saline, ethanol, or dimethylsulphoxide, and added in duplicate to the prp aliquots to produce a final concentration in the range of 0.1–30 µg/ml. When ethanol or dimethylsulphoxide was used to dissolve the compound, triplicate controls containing the same percentage of ethanol or dimethyl sulphoxide as the test compound was made. The final concentration of organic solvent was never greater than 0.1%, which has been determined to have no effect on TxB₂ generation.

Following a 10 min. incubation withtest compounds or controls, collagen was added to the tubes containing the test compounds to produce a final concentration of 20 µg/ml. The tubes were then whirly-mixed for 15 seconds and replaced in the dry bath for a further 10 minutes. Saline was added to the tubes containing the controls, in lieu of collagen. The reaction was then stopped by rapid centrifugation (15000 g for 3 mins). The plasma was removed and frozen at −29° C. until assayed.

(c) Assay of Thromboxane B₂

Aliquots (100 µl) of thromboxane TxB₂ (plasma extract or standards 50 to 10,000 pg/ml), [³H]-TxB₂ (approximately 15,000 dpm) and anti-TxB₂ antiserum (0.5 µg/100 µl) were combined in 50 mg phosphate buffer+0.1% gelatin+thimerosal (pH 6.8) were incubated for 16 hours at 4° C. The free and protein bound [³H]-TxB₂ were separated by absorption onto activated charcoal followed by centrifugation. 1.0 ml of the supernatant was added to an aqueous scintillation fluid, and the radioactivity present was counted in a liquid scintillation counter. The binding of [³H]-TxB₂ in the absence of added TxB₂ was approximately 55%. The minimum concentration of TxB₂ to be detected accurately in the plasma was 50 pg.ml. Cross reactivity with other prostaglandins was less than 0.005% except with PGD₂ wherein the cross reactivity was 1%.

The plasma samples were initially assayed to give approximation of TxB₂ content. The plasma was then appropriately diluted and re-assayed in duplicate to give final values.

(d) Analysis of Results

The amount of TxB₂ generated by collagen was calculated by subtracting mean values obtained for the saline stimulated platelets from the mean values obtained from the collagen stimulated platelets. The amount of TxB₂ generated in the presence of each concentration of test compound was expressed as a % of control and dose response curves were constructed to determine the concentration of test compound which produced 50% inhibition. These values known as the IC₅₀ obtained for various compounds of the present invention tested are represented in Table II below.

TABLE II

| COMPOUND (EXAMPLE NO.) | ACTIVITY (IC$_{50}$ × 10⁶ M) |
|---|---|
| 1 (Z-isomer) | 0.022 |
| 1 (E-isomer) | 0.89 |
| 2 (E-isomer) | 18.2 |
| 3 (Z-isomer) | 0.56 |
| 4 | 9.3 |
| 5 | 4.6 |
| 6 | 1.4 |
| 7 | 17.3 |
| 8 | 1.8 |
| 9 (Z-isomer) | 11.5 |
| 9 (E-isomer) | 403. |
| 10 (Z-isomer) | 1.71 |
| 10 (E-isomer) | 4.78 |
| 11 (Z-isomer) | 3.26 |
| 11 (E-isomer) | 21.8 |
| 12 (E-isomer) | 0.15 |

TABLE II-continued

| COMPOUND (EXAMPLE NO.) | ACTIVITY ($IC_{50} \times 10^6$ M) |
| --- | --- |
| 13 (Z-isomer) | 0.45 |

EXAMPLE 19

Whole Blood Aggregation and Thromboxane Formation In Vivo: Guinea Pig

All guinea pigs (albino male Dunkin-Bartley, 300–350 g) were fasted overnight before use in the test. The test compound was administered by oral dosing needle to conscious animals. All test compounds, if not water soluble, were administered formulated in a 50% PEG 400/50% carboxymethylcellulose mixture as solution or suspension. Oral dose volumes were 0.1 ml per 100 g body weight.

Animals were anaesthetized with pentabarbitone sodium (60 mg/kg) given intraperitoneally approximately 10 minutes before the bleed time. Once surgically anaesthetized, the peritoneal cavity was opened, and 4.5 ml blood was drawn into a syringe containing 0.5 ml 3.0% trisodium citrate (9:1 v/v) from the abdominal aorta via a 21/23 gauge butterfly needle. The blood was gently mixed with the citrate in the syringe, and transferred to a screwcap plastic tube. Animals were dosed and bled at one hour intervals.

Aggregation of the citrated guinea pig whole blood was carried out within 1–2 hours of bleeding, using standard whole blood aggregometry and counting technique. Aliquots (0.55 ml) of citrated whole blood were heated to 37° C. and stirred at 1000 RPM in an aggregometer. An initial 50 μl sample of blood was withdrawn for counting, collagen was added, and additional samples were withdrawn at 1, 2, 3 and 4 minutes. Aggregation was monitored by noting the decrease in single platelet count. Buffer (no collagen) control were included.

At the end of the four minute incubation for platelet counting, the remainder of each blood sample was allowed to stir for one additional minute. At 5 minutes, 1.0 μl of 19 mg/ml indomethacin (dissolved in dimethylsulfoxide) was added to each sample, resulting in a final indomethacin concentration of 30 ug/ml. The resulting solutions were mixed (15–30 seconds) and cooled on ice. Samples were centrifuged and 150 ul of plasma was removed. The plasma samples were frozen until radioimmunoassay for $TXB_2$. The radioimmunoassay was conducted as previously described at plasma dilutions of 1:20. Two vehicle administered control aminals were run. Groups of at least four animals per test compound were utilized.

Results (1) Platelet Counts

The raw data platelet counts (Isoton dilutions) are converted to whole blood platelet counts, and the fall in free platelet count (%) determined by computer analysis. Inhibition of aggregation was determined from these results, and was indicated by a decrease in platelet count during the 4 minute incubation. Inhibition of the platelet count fall in the early samples only (1 and 2 minutes) was taken as indicating an effect on rate rather than total extent of aggregation. Statistical analysis of control and test groups is by Student's t-test.

(2) Plasma $TXB_2$

The raw results obtained in the RIA from a 0.1 ml sample of 1:20 diluted plasma were corrected to pg/ml in original plasma sample ($\times 200$). The R.I.A. values were then normalized for initial platelet count within the blood sample to $5.0 \times 10^8$ ml$^{-1}$ (range of platelet count in citrated guinea pig whole blood was varied between the limits $2.8$–$7.0 \times 18^8$ ml$^{-1}$). The test and control results were then compared, and inhibition (%) calculated in the normal way. Statistical analysis is again by Student's t-test. The results obtained are illustrated in Table III.

TABLE III

| COMPOUND OF EXAMPLE NO. | % INHIBITION |
| --- | --- |
| 1 (Z-isomer) | −45.5 |
| 5 | −4.0 |
| 10 (E-isomer) | −18.6 |
| 11 (E-isomer) | −36.0 |
| 12 (E-isomer) | −92.3 |
| 13 (Z-isomer) | −49.1 |

Although this invention has been described with respect to specific modification, the details thereof are not to be construed as limitations, for it will be apparent that various equivalents, changes and modification may be resorted to without departing from the spirit and scope thereof and it is understood that such equivalent embodiments are intended to be included therein.

What is claimed is:

1. A compound of the formula

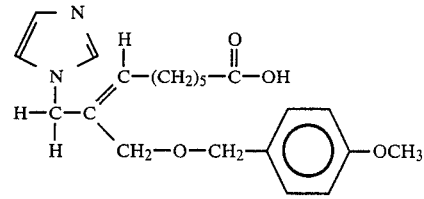

2. A compound of the formula:

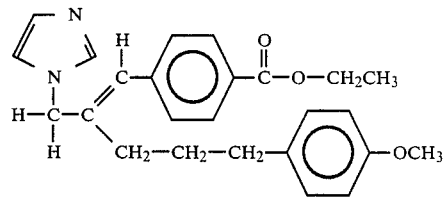

as the E-isomer.

* * * * *